United States Patent
Lazo

(10) Patent No.: US 11,510,614 B1
(45) Date of Patent: Nov. 29, 2022

(54) WEARABLE DEVICES AND SYSTEMS FOR PRESCRIPTION ADHERENCE

(71) Applicant: Express Scripts Strategic Development, Inc., St. Louis, MO (US)

(72) Inventor: Michael Lazo, Orlando, FL (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 423 days.

(21) Appl. No.: 16/700,447

(22) Filed: Dec. 2, 2019

(51) Int. Cl.
| | |
|---|---|
| *A61B 5/00* | (2006.01) |
| *A61J 7/04* | (2006.01) |
| *G16H 10/60* | (2018.01) |

(52) U.S. Cl.
CPC .......... *A61B 5/4833* (2013.01); *A61B 5/0022* (2013.01); *A61B 5/681* (2013.01); *A61J 7/0409* (2013.01); *G16H 10/60* (2018.01)

(58) Field of Classification Search
CPC ..... A61B 5/4833; A61B 5/0022; A61B 5/681; A61J 7/0409; G16H 10/60
See application file for complete search history.

(56) References Cited

U.S. PATENT DOCUMENTS

| | | |
|---|---|---|
| 4,223,801 A | 9/1980 | Carlson |
| 7,630,790 B2 | 12/2009 | Handfield |
| 7,941,325 B2 | 5/2011 | Heald |
| 8,926,542 B2 | 1/2015 | Gerber |
| 9,377,762 B2 | 6/2016 | Hoobler |
| 9,642,960 B2 | 5/2017 | Gerber |
| 10,025,908 B1 | 7/2018 | Orellano |
| 10,140,845 B1 | 11/2018 | Knas |
| 10,452,815 B2 | 10/2019 | Stewart |
| 2006/0124655 A1* | 6/2006 | Ratnakar ................. G07F 11/44 221/3 |
| 2010/0214877 A1 | 8/2010 | Turk |

(Continued)

FOREIGN PATENT DOCUMENTS

WO WO-2008064134 A2 * 5/2008 ............ A61J 7/0481

OTHER PUBLICATIONS

Lee, Iris. "Can Timer Cap put a lid on opioid epidemic? Moorpark firm finds abuse prevention market for a convenience product." San Fernando Valley Business Journal 22.17: 7(1). CBJ, L.P. (Aug. 21, 2017) (Year: 2017).*

*Primary Examiner* — Linh Giang Le
(74) *Attorney, Agent, or Firm* — Stinson LLP

(57) ABSTRACT

A wearable computing device for monitoring and facilitating prescription adherence by a patient is provided. The wearable computing device is in communication with an inventory management server. The wearable computing device includes a processor and a memory. The processor is configured to receive a set of prescription plan data including at least a prescription identifier and a prescription rate associated with the prescription identifier. The processor is further configured to determine an inventory level associated with the prescription identifier. The processor is also configured to determine, based at least on the prescription rate, a time value representing a period of time in which a patient is prescribed to take a pharmaceutical associated with the prescription identifier. The processor is additionally configured to present a prescription inventory indicator representing the inventory level. The processor is also configured to present a timer indicator representing the time value.

18 Claims, 17 Drawing Sheets

(56) References Cited

U.S. PATENT DOCUMENTS

| | | |
|---|---|---|
| 2015/0100335 A1* | 4/2015 | Englehard ......... A61M 15/0093 705/2 |
| 2015/0106221 A1 | 4/2015 | Tapley |
| 2015/0161353 A1 | 6/2015 | Emerson |
| 2015/0306340 A1 | 10/2015 | Giap |
| 2016/0324727 A1 | 11/2016 | Waugh |
| 2017/0076065 A1 | 3/2017 | Darr |
| 2017/0322908 A1 | 11/2017 | Bin |
| 2018/0036591 A1 | 2/2018 | King |
| 2018/0366216 A1 | 12/2018 | Gershfang |
| 2019/0035499 A1 | 1/2019 | Daya |
| 2019/0354410 A1 | 11/2019 | Baldasaro |

\* cited by examiner

WEARABLE DEVICES AND SYSTEMS FOR PRESCRIPTION ADHERENCE

FIELD OF INVENTION

The field relates to systems and methods for prescription adherence in patients, and wearable electronic devices related systems and methods used to promote prescription adherence.

BACKGROUND OF THE DISCLOSURE

In the context of pharmaceutical, patient adherence quality to prescription plans can have significant ramifications. Generally, a patient may be prescribed a dosage level of a particular pharmaceutical (e.g., a number of pills, a volume of liquid drugs, or a number of inhalations of a gaseous drug) over a particular period of time. Further, in many cases prescriptions entitle a patient to obtain a certain number of refills of the pharmaceutical before the patient is required to obtain a new prescription.

Because pharmaceuticals are often expensive and used in urgent or life-saving care, tracking the usage levels of pharmaceuticals is important to patients, pharmaceutical distributors, and health care providers. But, although the prescriptions set forth a defined usage level and rate for pharmaceuticals, in many cases patients do not follow the prescription plan properly. Patients may fail to follow the prescription plan for a variety of reasons including, for example, scheduling difficulties, and discomfort with taking the pharmaceutical, forgetfulness, or misplacement of the pharmaceutical.

When patients fail to take pharmaceuticals at the prescribed rate and dosage, the patients, pharmaceutical distributors, and health care providers may all experience adverse consequences. Most importantly, the patient may experience side effects from taking the pharmaceutical at the wrong rate. In some cases, where the pharmaceutical is associated with critical care, a patient may become ill or even die if the pharmaceutical is not taken at the prescribed rate or dosage. Further, if the patient is not taking pharmaceuticals at the appropriate rate, the health care provider may have an improper understanding of their patient's care.

Additionally, where a pharmaceutical prescription is associated with a mail-order refill, a patient's failure to adhere to a prescription plan may have adverse impacts. For example, inventory management servers associated with such mail-order refill services presume patient adherence to a prescription plan. Where patients fail to adhere to the prescription plan, the mail-order refill systems may receive improper input and instruct that a patient be sent a refill at an improper time. In such cases, the refill may therefore arrive untimely such that a patient fails to receive the pharmaceutical when needed, or such that the prescription may be wasted.

As such, systems and methods for monitoring prescription adherence are desirable to determine how a patient is adhering to a prescription plan.

BRIEF SUMMARY OF THE INVENTION

In one aspect, a method for monitoring prescription adherence is provided. The method is performed by a wearable computing device in communication with an inventory management server. The wearable computing device includes a processor and a memory. The method includes receiving a set of prescription plan data including at least a prescription identifier and a prescription rate associated with the prescription identifier. The method also includes determining an inventory level associated with the prescription identifier. The method additionally includes determining, based at least on the prescription rate, a time value representing a period of time in which a patient is prescribed to take a pharmaceutical associated with the prescription identifier. The method further includes presenting a prescription inventory indicator representing the inventory level. The method also includes presenting a timer indicator representing the time value.

In another aspect, a wearable computing device is provided. The wearable computing device is in communication with an inventory management server. The wearable computing device includes a processor and a memory. The processor is configured to receive a set of prescription plan data including at least a prescription identifier and a prescription rate associated with the prescription identifier. The processor is further configured to determine an inventory level associated with the prescription identifier. The processor is also configured to determine, based at least on the prescription rate, a time value representing a period of time in which a patient is prescribed to take a pharmaceutical associated with the prescription identifier. The processor is additionally configured to present a prescription inventory indicator representing the inventory level. The processor is also configured to present a timer indicator representing the time value.

In yet another aspect, a prescription adherence system for monitoring and facilitating prescription adherence by a patient is provided. The prescription adherence system includes an inventory management server and a wearable computing device. The inventory management server includes a server processor and a server memory. The wearable computing device is in networked communication with the inventory management server, and the wearable computing device includes a device processor and a device memory. The device processor is configured to receive a set of prescription plan data including at least a prescription identifier and a prescription rate associated with the prescription identifier. The device processor is also configured to determine an inventory level associated with the prescription identifier. The device processor is further configured to determine, based at least on the prescription rate, a time value representing a period of time in which a patient is prescribed to take a pharmaceutical associated with the prescription identifier. The device processor is additionally configured to present a prescription inventory indicator representing the inventory level. Moreover, the device processor is configured to present a timer indicator representing the time value.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
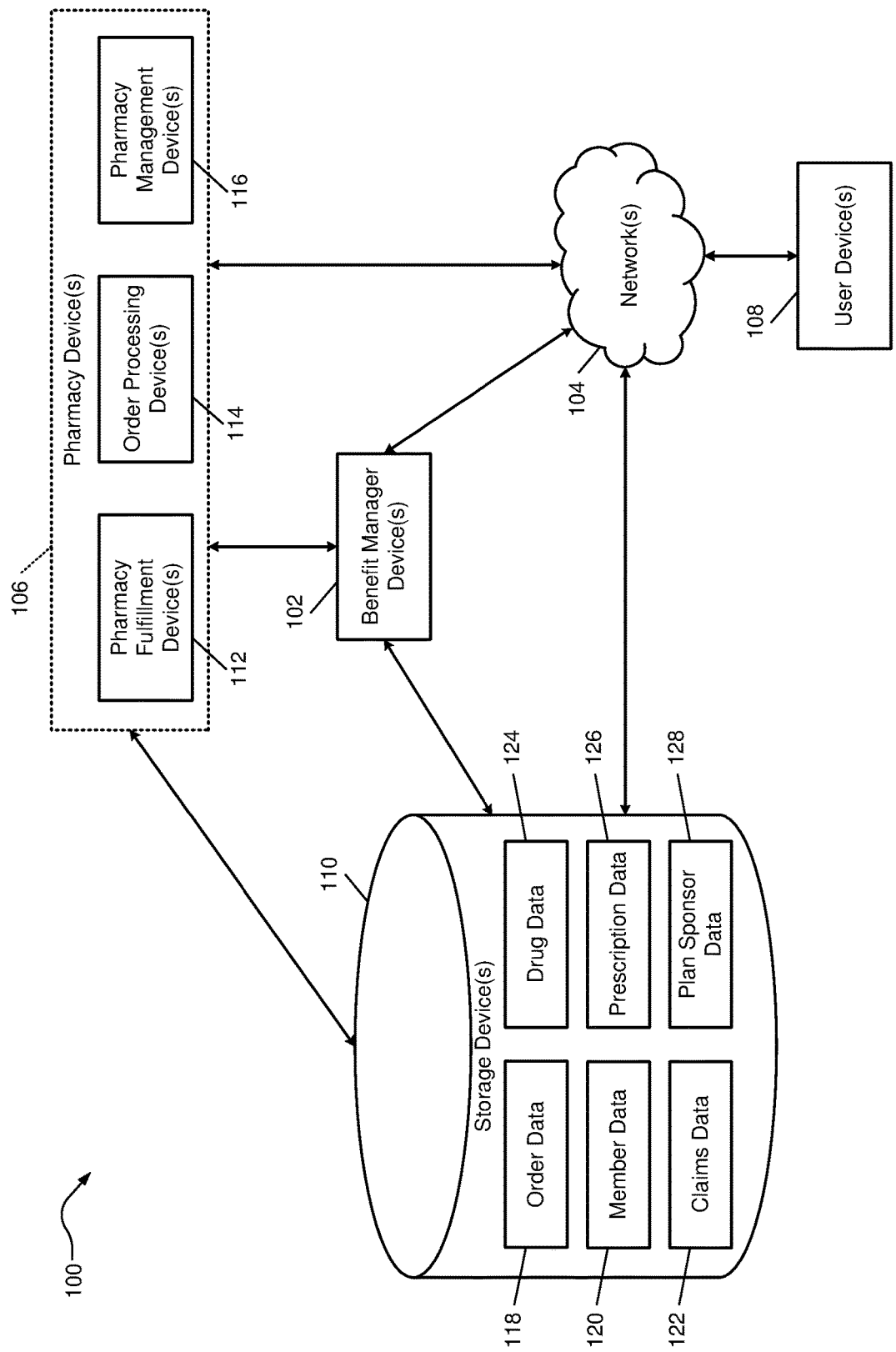
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Patient adherence to pharmaceutical prescriptions is a crucial aspect of healthcare delivery. As used herein, when a patient takes pharmaceuticals in a manner consistent with their prescribed use, the patient "adheres" to the prescription or may be said to be "adherent". When patients take pharmaceuticals in a manner inconsistent with their prescriptions, such patients are "not adherent" and may be exposed to risks from under-medication or overmedication, and any associated side effects or consequences. There are a wide variety of reasons that patients may fail to adhere to their prescriptions ranging from a reluctance to take the medication, to discomfort or side effects from the medication to a lack of understanding of the prescription. Because of such risks, reliable means of monitoring and facilitating adherence are desirable.

Patient adherence is also important in the context of high-volume pharmacies or fulfillment centers (for example, a mail order pharmacy, a direct delivery pharmacy, etc.) Such pharmacies or centers depend upon expected patient adherence and usage to determine appropriate times to provide refills. However, as described herein, patient adherence is difficult to predict and may vary significantly across patients. As a result, pharmacies and centers are often lack access to critical data that may be used to process pharmacy refills and fulfillment requests in an appropriate manner. The absence of reliable data regarding adherence makes it difficult or impossible for pharmacies and centers to properly manage inventory and process orders. Additionally, refilling or renewing a prescription at the appropriate time can ensure that the patient has the appropriate supply of the medication available at the correct time. This should also assist in maintaining adherence to the drug therapy regimen.

The systems and methods described address these known problems by providing a prescription adherence system including a wearable computing device configured to facilitate and monitor prescription adherence, and to provide improved adherence data to inventory management servers. Specifically, the wearable computing devices described herein are configured to present user interfaces that accurately track patient prescription adherence, alert patients to a need to take a prescription, receive input on prescription adherence, and allow patients to request refills of pharmaceuticals or renewals of prescriptions.

The systems and methods described herein also provide accurate and current data regarding patient adherence to inventory management servers to improve inventory management and order processing. Further, in some embodiments, the systems and methods described allow for a patient to make direct requests for refills of pharmaceuticals or requests to renew prescriptions. As such, embodiments of the systems and methods described address a known technological problem in pharmacies and fulfillment centers by addressing unavailability of accurate information on patient adherence to prescriptions. Embodiments of the systems and methods described solve this problem by employing a technological solution of monitoring and facilitating patient adherence using a wearable computing device, and relaying monitored information to computing systems including inventory management servers used to process and fulfill prescription orders. Further, the systems and methods described utilize wearable computing devices that provide improved availability of adherence to patients, and thereby reliably facilitate and monitor patient adherence in a variety of contexts.

The methods described are performed by a prescription adherence system for monitoring and facilitating prescription adherence by a patient. The prescription adherence system includes an inventory management server and a wearable computing device. The inventory management server includes a processor and a memory and is configured to manage and process pharmaceutical orders, and to ensure fulfillment of such orders. The inventory management server may be representative of any suitable computing server including servers typically utilized in enterprise data centers. The inventory management server is also capable of communicating directly or indirectly with external devices including but not limited to the wearable computing device and other user computing devices. As such, the inventory management server includes a communications interface that can access external networks, computer communication network, and the Internet. Because of its role in fulfillment of pharmaceutical orders, the inventory management server stores information for each prescribed pharmaceutical associated with each patient along with fulfillment information. In the example embodiment, the inventory management server tracks when each pharmaceutical is provided to a user. Further, as described herein, the inventory management server may synchronize with the wearable computing device to regularly track the inventory of each pharmaceutical available to each user.

The wearable computing device includes a processor and a memory and is in communication with at least the inventory management server. In the example embodiment, the wearable computing device is a "smart watch" including, for example, an Apple Watch, a Samsung Smartwatch, or any other known smart watches capable of functioning in the manner described herein. The wearable computing device includes a touchscreen graphical display configured to provide graphical user interfaces and receive user inputs. The wearable computing device also may include components and methods for tracking location and orientation including, for example, gyroscope, an accelerometer, and a position detector, and may be configured to receive and capture other user information including location data and orientation data. The wearable computing device may further be configured to receive audio input through an interface such as a microphone, and to present audio output through a speaker. The wearable computing device may additionally be configured to capture user biometric information including but not limited to heart rate and electrocardiogram data. In some examples, the wearable computing device may be configured to capture user body temperature, blood pressure, and blood glucose levels. The wearable computing device is additionally configured to communicate directly or indirectly with external devices including but not limited to the inventory management server and other user computing devices. In the example embodiment, the wearable computing device includes a communications interface configured to provide wireless communication to such devices. The wearable computing device may utilize any suitable wireless protocol for communications including but not limited to cellular communications, Bluetooth® connectivity, WiFi, near field communication (NFC), and Zigbee. In some examples, the wearable computing device is also configured to communicate through wired networking protocols.

In the example embodiment, the wearable computing device is configured to execute a mobile application ("wearable app") that provides the interfaces and methods described herein. In some embodiments, the wearable app is associated with a related application that is available on other user computing devices. In one example, the related application ("mobile app") is available on mobile computing devices including smartphones or tablet computing devices. As described herein, the mobile app may be used to present information that may not easily be provided on a smartwatch or other wearable computing devices, and similarly receive information that may not easily be received on a smartwatch or other wearable computing devices. As such, in these embodiments, the mobile app may be used to facilitate some of the methods described. For example, the mobile app may allow a user to configure the presentation of the user interfaces described and to facilitate user authentication for certain parts of the methods described.

As described herein, the wearable app presents information and interfaces related to user prescriptions. The information presented may include, for example, the number of doses available for a particular prescription, the number of refills available for a particular prescription, the amount of time remaining before the user is prescribed to take a next dose of a particular prescription, an alert indicating that a next dose of a particular prescription should be taken, and other user alerts. The interfaces may include a confirmation screen to confirm whether a user has taken a next dose of a particular prescription, a refill interface allowing a user to request a refill of a particular prescription, and a renewal interface allowing a user to request a renewal of a particular prescription. In some embodiments, the wearable app is further configured to present such information and interfaces for multiple pharmaceutical prescriptions. In the example embodiment, the information and interfaces for each of the multiple pharmaceutical prescriptions can be distinguished by color coding. Color coding may be useful to protect the privacy of user healthcare data by avoiding the presentation of the name of prescribed drugs. Color coding may also simplify the presentation of information on the wearable computing device, and make the wearable app more usable for the user. In the example embodiment, a user may configure the color coding and display settings of the wearable app by using the mobile app on another user computing device such as a mobile computing device. In other examples, the user may configure the color coding on the wearable app itself. In additional examples, the user may configure the color coding through use of another computing system in communication with the wearable app or via a web interface. In further examples, user may configure the presentation of the user interfaces in other ways including, for example, configuring specific indicator widths and indicator textures for particular prescriptions based on user preferences.

The color coding approach protects the security of patient health information because the user interfaces described present information in the form of abstracted shapes in customized colors based on personal selections made by each patient. In the example embodiment, the user interfaces do not present the names of prescriptions or the dosages of prescriptions in a textual form. As such, third-parties without knowledge of patient configuration selections cannot determine what the indicators of the user interfaces represent. As such, the configuration tools described (whether on the mobile app or through other similar means) provide an abstraction layer that protects patient health information and prevents disclosure of such information to third-parties.

Further, in some examples, requests for refills or renewals on the wearable app may require secondary authentication. In such examples, a user may initially select a renewal or refill on the wearable app before being prompted to authenticate the renewal or refill request on the mobile app. As explained herein, authentication may be performed using any suitable method including, for example, a personal identification number (PIN), a password, a challenge phrase, two-factor authentication, or biometric authentication such as fingerprint or retinal scan. In other examples a user may authenticate a renewal or refill on the wearable app using similar authentication methods.

In the example embodiment, the wearable computing device receives a set of prescription plan data including at least a prescription identifier and a prescription rate associated with the prescription identifier. Specifically, the wearable computing device receives, directly or indirectly, information related to pharmaceutical prescriptions prescribed to a user. The information identifies each prescription via the prescription identifier. The prescription identifier may be the name, serial number, or other identifier sufficient to specifically identify each prescription associated with the set of prescription plan data. (However, as explained herein, each prescription may be presented on the wearable app to the user via color coding without listing the name of each prescription on the wearable app interface.) The prescription rate identifies the frequency with which each prescription should be taken. In the example embodiment, the set of prescription plan data may include information for multiple prescriptions because at least some users may have multiple prescription plans to which they wish to adhere. As explained herein, where users have high numbers of prescriptions, the wearable app may display information and interfaces for the prescriptions over multiple screens. The layout and order used to present multiple prescriptions may be controlled using a configuration screen on the wearable app or the mobile app.

In some examples, the set of prescription plan data may also include other information relevant to the prescriptions including, for example, dosage levels and instructions. As described below, in such examples, such information may be presented when a user is prompted to take a particular pharmaceutical. The information may specify, for example, the exact dose prescribed to be taken at a particular time in terms of pill counts, volume (in the case of liquid pharmaceuticals), and spray pumps (in the case of inhaled pharmaceuticals). The information may also specify any required steps a patient should take when taking a pharmaceutical such as, for example, drinking liquids or eating food.

In the example embodiment, the set of prescription plan data is received, directly or indirectly, from the inventory management server. In other examples, the set of prescription plan data may be received from any suitable data source including, for example, other user computing devices such as the mobile computing device, or a server associated with a pharmacy, insurer, or healthcare provider. In one example, the wearable computing device may receive the set of prescription plan data through a "push" from an external system such as the inventory management server. In another example, the wearable computing device may initiate a "pull" request to the external system, which results in transmission of the set of prescription plan data to the wearable computing device.

The systems and methods described herein are further designed to ensure that the 1 patient data is kept secure, private, and confidential as necessary according to any appropriate regulations or laws including the Health Insurance Portability and Accountability Act (HIPAA). As such, any data related to prescriptions stored on the wearable computing device, the inventory management server, and any other computing device is appropriately stored and transmitted using appropriate security and encryption.

The wearable computing device also determines an inventory level associated with each prescription identifier specified in the set of prescription plan data. Initially, when a user receives a particular prescription for the first time, the inventory management server identifies that the particular prescription has a "full" inventory level with the maximum amount of doses associated with the particular prescription. Therefore, initially, the wearable computing device is configured to receive the inventory level from the inventory management server for a particular prescription. Thereafter, the wearable computing device locally tracks the consumption of each prescription specified in the set of prescription plan data by receiving user inputs when a prescribed pharmaceutical is taken by the user. In the example embodiment, each time the wearable computing device receives a user input indicating a pharmaceutical has been taken, the wearable computing device may synchronize with the inventory management server and the user computing device.

The wearable computing device also determines a time value representing a period of time in which a patient is prescribed to take a pharmaceutical associated with the prescription identifier. The wearable computing device determines the time value based on at least the prescription rate. In operation, initially and after each time a user indicates that a particular prescription has been taken, the wearable computing device determines when the user is prescribed to next take the particular prescription. In other words, the wearable computing device utilizes a timer to count the time when the user is prescribed to next take the particular prescription.

The wearable computing device presents a prescription inventory indicator representing the inventory level for each prescription specified in the set of prescription plan data. In other words, the wearable computing device is configured to present the volume of remaining inventory for each prescription on the user interface of the wearable app.

The wearable computing device also presents a timer indicator representing the time value for each prescription specified in the set of prescription plan data. In other words, the wearable computing device is configured to present the time remaining before the user is prescribed to next take each prescription specified in the set of prescription plan data.

In operation, when the wearable computing device determines that the time value has dropped to zero for a particular prescription, the wearable computing device is configured to present an alert to prompt the user to take the next dose of the particular prescription. In operation, the wearable computing device determines that the time value indicates that the patient is prescribed to take the pharmaceutical immediately because the time value is at zero or has passed zero. When the wearable computing device determines that the patient is prescribed to take the pharmaceutical immediately, the wearable computing device presents an adherence user interface configured to receive input to confirm whether the patient has taken the pharmaceutical. As described below, the adherence user interface allows a user to affirm that they have taken the pharmaceutical or that they have not taken it. The wearable computing device also receives input from the user confirming whether the patient has taken the particular pharmaceutical. In some examples, the adherence user interface may also allow a user to select a "hold" or "snooze" option to allow the user more time to adhere to the prescription.

Depending on the user response to the adherence user interface, the wearable computing device updates the inventory level for the particular pharmaceutical for which the user is prompted. If the wearable computing device receives input indicating that the patient has taken the particular pharmaceutical, the wearable computing device determines that such input was provided and decrements the inventory level for the particular pharmaceutical based on such input. The wearable computing device also resets the time value to the period of time associated with the prescription rate, presents a prescription inventory indicator representing the inventory level, and presents a timer indicator representing the time value. In other words, after the wearable computing device receives input indicating that the patient adhered to the prescription for a particular pharmaceutical, the user interface of the wearable app is updated to show a decremented inventory level (reflecting the consumption of the prescribed pharmaceutical) and a reset timer (reflecting that the user is prescribed to wait for the full prescribed time period before taking the next dose of the particular prescribed pharmaceutical.)

Conversely, if the wearable computing device receives input indicating that the patient has not taken the particular pharmaceutical, the wearable computing device determines that such input was provided, transmits an alert message, presents a prescription inventory indicator representing the inventory level, and presents a timer indicator representing the time value. Notably, the wearable computing device does not decrement the prescription inventory indicator or reset the timer indicator when the wearable computing device receives input indicating that the patient has not taken the particular pharmaceutical. Rather, the wearable computing device will continue to indicate that the prescription specifies that the user is scheduled to take the particular pharmaceutical. In the example embodiment, the alert message is transmitted to the inventory management server to note that the patient did not timely adhere to the prescription. In some examples, the alert message is also transmitted to the user to warn the user that they have not adhered to the prescription. In other examples, the alert message may be transmitted to a healthcare provider to alert about the failure to adhere to the prescription.

As described above, in some examples, the wearable computing device is configured to synchronize with the inventory management server. In further examples, the wearable computing device may synchronize with other systems including the user computing system. In the example embodiment, the wearable computing device synchronizes the inventory level. In some examples, any appropriate data may be synchronized including the set of prescription plan data and any adherence information provided by the user including, for example, user input regarding adherence and the timing of such input.

In some examples, the wearable computing device provides interfaces allowing a user to request a refill of a particular prescription or a renewal of a particular prescription. Generally, pharmaceutical prescriptions may be associated with a certain amount of refills that allow a patient to receive a certain amount of new pharmaceuticals without a new prescription. Typically, the amount of refills available for a prescription is a specified numeric amount.

In one example, the wearable computing device presents a refill user interface configured to receive a refill input requesting a resupply of the prescription associated with the prescription indicator. In some cases, the refill user interface may be presented with an indicator displaying the amount of remaining refills available for the particular prescription. In other cases, the refill user interface may be displayed only when the inventory level of the particular prescription falls below a certain threshold. For example, when the inventory level falls to a level such that the user will run out of the particular pharmaceutical within a week or fifteen days or any other suitable period (assuming the user adheres to the prescription), the refill user interface may be displayed. Upon receiving a refill input, the wearable computing device transmits a refill request to the inventory management server. The inventory management server processes the refill request. Upon fulfilling the refill request, the inventory management server updates the inventory level for the particular pharmaceutical to reflect the fact that the user now has new pharmaceuticals available. The wearable computing device receives an inventory update from the inventory management server. The inventory update reflects the new inventory level for the particular pharmaceutical that reflects the newly available pharmaceuticals and the decremented amount of available refills. The inventory update may be "pushed" by the inventory management server or "pulled" by the wearable computing device. The wearable computing device revises the inventory level based on the inventory update to show the newly available inventory. If the user has used all of the previously available prescriptions (prior to the arrival of the refill), the inventory level will reflect a "full" amount of prescriptions based on one refill. If the user has not used all of the previously available prescriptions, the inventory level may reflect an "overfill" amount indicating the total amount of doses available to the user. The wearable computing device presents the prescription inventory indicator representing the revised inventory level.

As specified above, when a user requests a refill through the refill user interface, the wearable computing device may request that the user authenticate the request. Authentication may be useful, for example, because the user may be charged financially for the refill. In some examples, the user may authenticate the request on the wearable computing device using any suitable method including but not limited to authenticating using a personal identification number (PIN), a password, a challenge phrase, two-factor authentication, or biometric authentication such as fingerprint or retinal scan. In other examples, the wearable app may determine that authentication is required and alert the user to authenticate using the mobile app on a secondary device such as a mobile computing device.

In some examples, the wearable computing device may also allow a user to request a renewal of a particular prescription. Generally, a user may seek to request a renewal of a prescription when the user is low on refills or out of refills for a particular prescription. In the example embodiment, the wearable computing device may determine that the inventory level reflects that a user is low on inventory for a particular pharmaceutical and has no remaining refills. In such examples, the wearable computing device confirms that a renewal is an available option based on the set of prescription plan data and, if so, displays a renewal user interface. In one example, the renewal user interface allows a user to select a renewal request. When the wearable computing device determines that a renewal request is made, the wearable computing device initiates a renewal procedure. In some cases, the renewal request may require further information and the wearable computing device prompts the user to access the mobile app on a computing device such as the mobile computing device.

The wearable app described herein may be presented in any suitable layout. In the drawings, two primary user interfaces for the wearable app are disclosed, but any suitable variation or alternative user interfaces may be used to provide the systems and methods disclosed herein. A first example user interface is adapted for use on a user interface such as a Samsung Galaxy Smartwatch. A second example user interface is adapted for use on a user interface such as an Apple Watch.

Described herein are several use cases provided by the wearable computing device via the wearable app. Notably, the wearable computing device facilitates at least five distinct methods for monitoring and promoting prescription adherence. In a first example, the wearable computing device is configured to provide inventory and timing information for a plurality of prescriptions. More specifically, the wearable computing device receives a set of prescription plan data for a plurality of prescriptions including prescription identifiers and prescription rates for each prescription identifier. The wearable computing device determines, for each prescribed pharmaceutical, an inventory level and a time value indicating a period of time in which the patient is prescribed to take each prescribed pharmaceutical. The wearable computing device displays (or presents) an inventory indicator representing the inventory level for each prescribed pharmaceutical and a time indicator representing the time value for each prescribed pharmaceutical. In this use case, the wearable computing device regularly updates a user about the status of each of her or his prescribed prescriptions that are tracked by the wearable computing device. In some cases, a user may have enough prescriptions to cause the wearable computing device to display prescription inventories and timer indicators over multiple display screens through which a user may toggle or scroll. The user may configure the order and orientation of such prescription inventories and timer indicators based on user preference. In the example embodiment, the user configures the order and orientation through use of the mobile app. In other embodiments, the user may configure the order and orientation using the wearable app.

In a second example, the wearable computing device tracks adherence and records adherence. Specifically, the wearable computing device is configured to track the time value and prompt a user to take each prescription at an appropriate time as determined by each prescription rate. The wearable computing device also prompts the user for adherence feedback through an adherence user interface that indicates whether a user has taken a prescription at the prompted time. If the user adheres to the prescription and indicates the same through the adherence user interface, the wearable app tracks the adherence, decrements the inventory level accordingly, and presents an updated prescription inventory indicator and a reset timer indicator. The wearable app may also communicate the adherence to the inventory management server or other computing devices including the mobile computing device. If the user fails to adhere to the prescription and indicates the same through the adherence user interface, the wearable app tracks the failed adherence, transmits an alert, presents the inventory indicator without a change (i.e., without decrementing), and presents the timer indicator to remind the user that a prescription should still be taken promptly. The wearable app may transmit the alert to any suitable recipient including the inventory management server or a healthcare provider. In some cases, when the wearable computing device prompts the user to take a particular prescribed pharmaceutical, the wearable computing device may provide appropriate dosage instructions or recommendations associated with the prescription such as drinking fluids or eating.

In a third example, the wearable computing device may track adherence without prompting the user for adherence feedback. For example, a user may wish to take a prescription within an appropriate window of time, but before the timer indicator reaches zero. In such examples, the user may select an adherence interface icon for the appropriate prescription and provide input indicating that the user has adhered to the particular prescription. In such cases, the wearable computing device receives adherence feedback indicating that the patient adhered to the particular prescription, decrements the inventory level accordingly, and presents an updated prescription inventory indicator and a reset timer indicator. The wearable app may also communicate the adherence to the inventory management server or other computing devices including the mobile computing device.

In a fourth example, the wearable computing device presents a refill user interface that allows a user to place a refill order. In one example, the wearable computing device presents the refill user interface on the wearable app at all times and the user may select it at any time. In another example, the wearable computing device presents the refill user interface after determining that the associated inventory level has fallen below a predefined renewal threshold indicating that the user has a limited amount of prescription pharmaceutical inventory available. In some cases, the predefined renewal threshold may be associated with the time to provide or ship a refill, and therefore set to ensure that a user that requests a timely refill does not run out of prescriptions while waiting for a refill. For example, the predefined renewal threshold may be calculated by the wearable computing device and/or the inventory management server based on the expected shipping time associated with the refill, the current inventory level, and the prescription rate. The wearable computing device presents the refill user interface such that, when a user requests a refill, an order is transmitted to the inventory management server and an order is recorded and noted on both the inventory management server and on the wearable computing device. When the inventory management server receives the refill order, in some examples it transmits a confirmation to the wearable computing device and other associated devices that indicates that the order fulfillment is in progress. The wearable computing device is also configured to present the amount of available refills on or in conjunction with the presentation of the refill user interface. When the confirmation of order fulfillment is received by the wearable computing device, the wearable computing device decrements the amount of available refills available and revises the refill user interface to present a decremented amount of available refills.

In a fifth example, the wearable computing device is configured to allow a user to request a renewal of a prescription through the use of a renewal user interface. In one example, the wearable computing device presents the renewal user interface on the wearable app at all times and the user may select it at any time. In another example, the wearable computing device presents the renewal user interface after determining that the amount of available renewals has fallen below a predefined renewal threshold. In the example embodiment, the wearable computing device presents the renewal interface when the amount of available refills is at one or fewer. The wearable computing device presents the renewal user interface to allow a renewal request. When the renewal user interface receives a renewal request, the wearable computing device transmits a confirmation request to the inventory management server to confirm that a renewal of the prescription is available. When the inventory management server confirms that a renewal of the prescription is available, the user may complete a request for renewal. In some examples, the wearable computing device redirects a user to the mobile computing device or another suitable device so that the user may complete the request for renewal on the mobile app. If the inventory management server determines a renewal of the prescription is not available, it transmits an unavailability message to the wearable computing device. If the wearable computing device receives an unavailability message, the wearable computing device causes the wearable app to present an alert to the user indicating that no renewals are available.

The described use cases are presented for illustrative purposes. In other examples, other use cases of the systems and methods described herein may be provided by combining or adapting any of the described steps or any of the described examples together.

In some examples the user interfaces on the wearable computing device may display an icon interface that can be configured (using the mobile app or any suitable interface) to be color coded and associated with a prescription as selected by a user. In one example, the icon interface is configured to allow a tap input (i.e., via a tap on the touchscreen at the location of the icon interface) which indicates that the user has taken a prescription associated with the color coded icon. The icon indicator may be used with the other interfaces described and, for example, when an input is received, the associated inventory level for the prescription is decremented.

Generally, the systems and methods described herein are configured to perform at least the following steps that may be performed in any order, and using any permutation of such steps: receive a set of prescription plan data including at least a prescription identifier and a prescription rate associated with the prescription identifier; determine an inventory level associated with the prescription identifier; determine, based at least on the prescription rate, a time value representing a period of time in which a patient is prescribed to take a pharmaceutical associated with the prescription identifier; present a prescription inventory indicator representing the inventory level; present a timer indicator representing the time value; determine that the time value indicates that the patient is prescribed to take the pharmaceutical immediately; present an adherence user interface configured to receive input to confirm whether the patient has taken the pharmaceutical; receive input from the user confirming whether the patient has taken the pharmaceutical; determine, based on the input, that the patient has taken the pharmaceutical; decrement the inventory level based on the input; reset the time value to the period of time associated with the prescription rate; present the prescription inventory indicator representing the inventory level; present the timer indicator representing the time value; determine, based on the input, that the patient has not taken the pharmaceutical; transmit an alert message; present the prescription inventory indicator representing the inventory level; present the timer indicator representing the time value; synchronize the time value and the inventory level with the inventory management server; present a refill user interface configured to receive a refill input requesting a resupply of the prescription associated with the prescription indicator; upon receiving the refill input, transmit a refill request to the inventory management server; receive an inventory update from the inventory management server; revise the inventory level based on the inventory update; and present the prescription inventory indicator representing the inventory level.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, a wearable electronic device, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/ or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 can also include a unique identifier for the wearable device associated with a patient. In an example, the member data 120 identifies the patient wearable device. In an example, the member data 120 identifies the caregiver's wearable device, with the caregiver being identified as caring for a patient receiving the medication. In an example, the member data 120 identifies the parent's device or guardian's wearable device, with the parent or guardian being identified as caring for a minor patient receiving the medication. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc. The message preferences can include types of indicators to be displayed on the wearable device as described herein. The message preferences can include the length, width and color of the indicators to be displayed on the wearable device. In an example embodiment, the default indicators are color coded to match the color of the individual drugs, e.g., pills, tablets, capsules and the like, being filled at the pharmacy 106.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably. In some instances the patient may be a user who is a dependent of the member.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in a solid form, e.g., pill form, tablet form, capsule form or the like), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Each of the devices 102, 104, 106, 108 and 110 may be a source of an anomaly, which can be analyzed by the anomaly analyzer and methods described herein.

Figure 2:
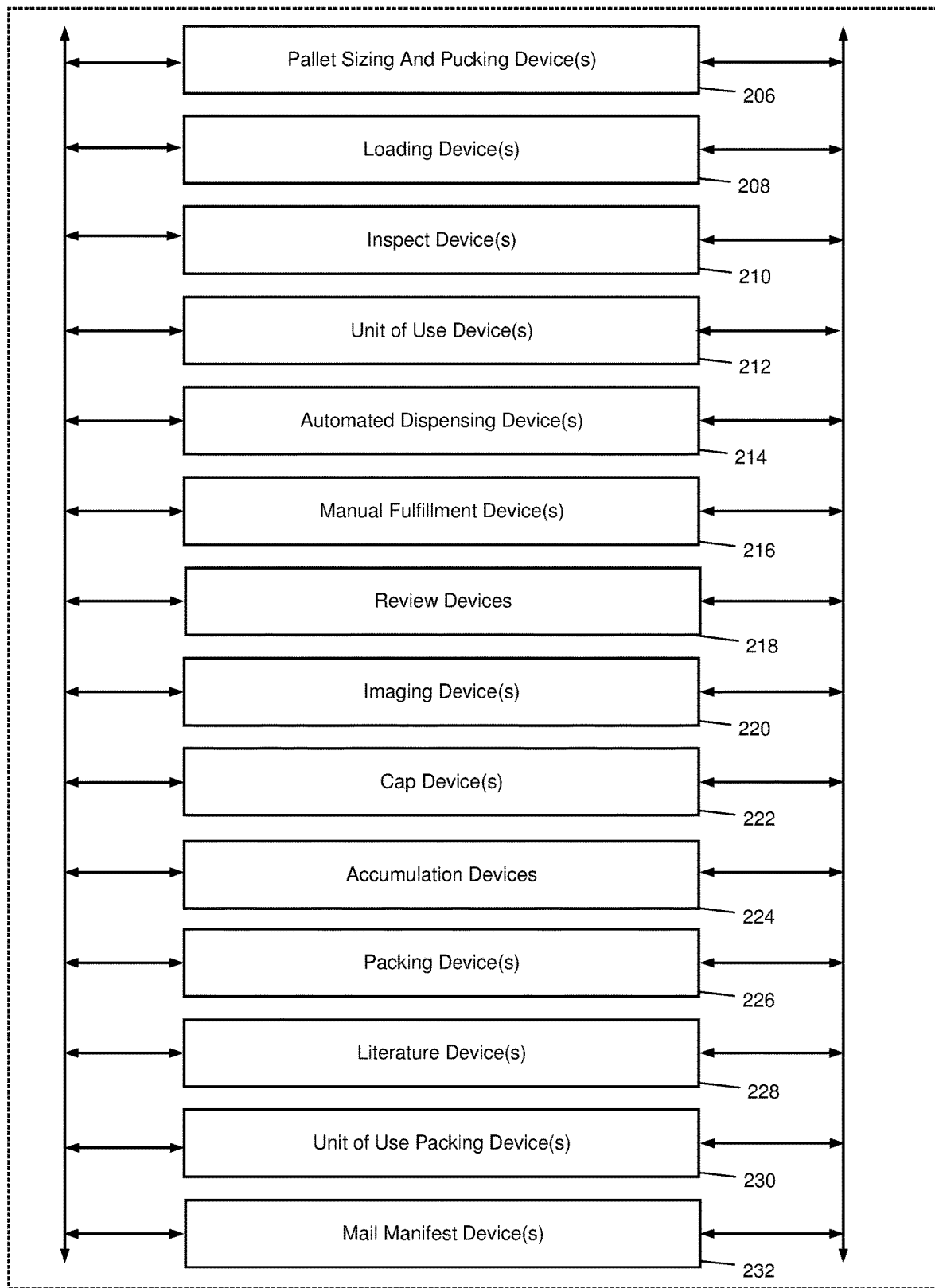
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Each of the devices in the pharmacy fulfillment device 112 may be a source of an anomaly, which can be analyzed by the anomaly analyzer and methods described herein.

Figure 3:
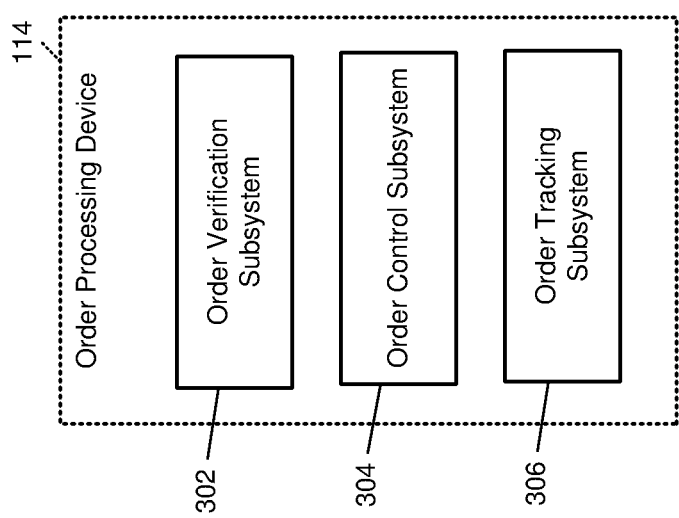
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Each of the subsystems 302, 304, or 306 in the order processing device 114 may be a source of an anomaly, which can be analyzed by the anomaly analyzer and methods described herein.

Figure 4:
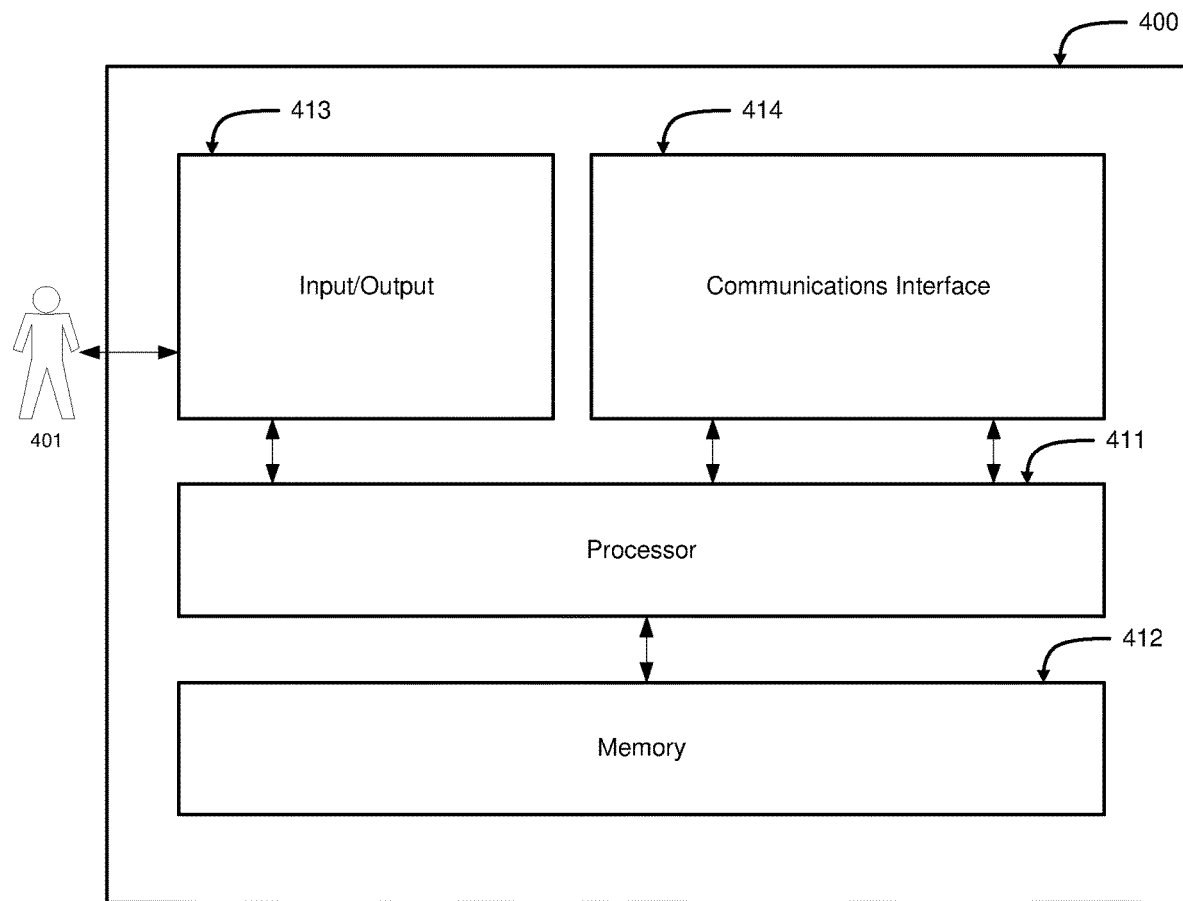
FIG. 4 is a functional block diagram of an example computing device that may be used in the environments described herein.

FIG. 4 is a functional block diagram of an example computing device 400 that may be used in the environments described herein. Specifically, computing device 400 illustrates an exemplary configuration of a computing device. Computing device 400 illustrates an exemplary configuration of a computing device operated by a user 401 in accordance with one embodiment of the present invention. Computing device 400 may include, but is not limited to, a wearable computing device, a mobile computing device, a user computing device, an inventory management server, a host device, an inventory device, and any other system described herein. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of monitoring and facilitating prescription adherence by a patient, as described herein. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively coupleable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, LTE, 5G or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

Figure 5:
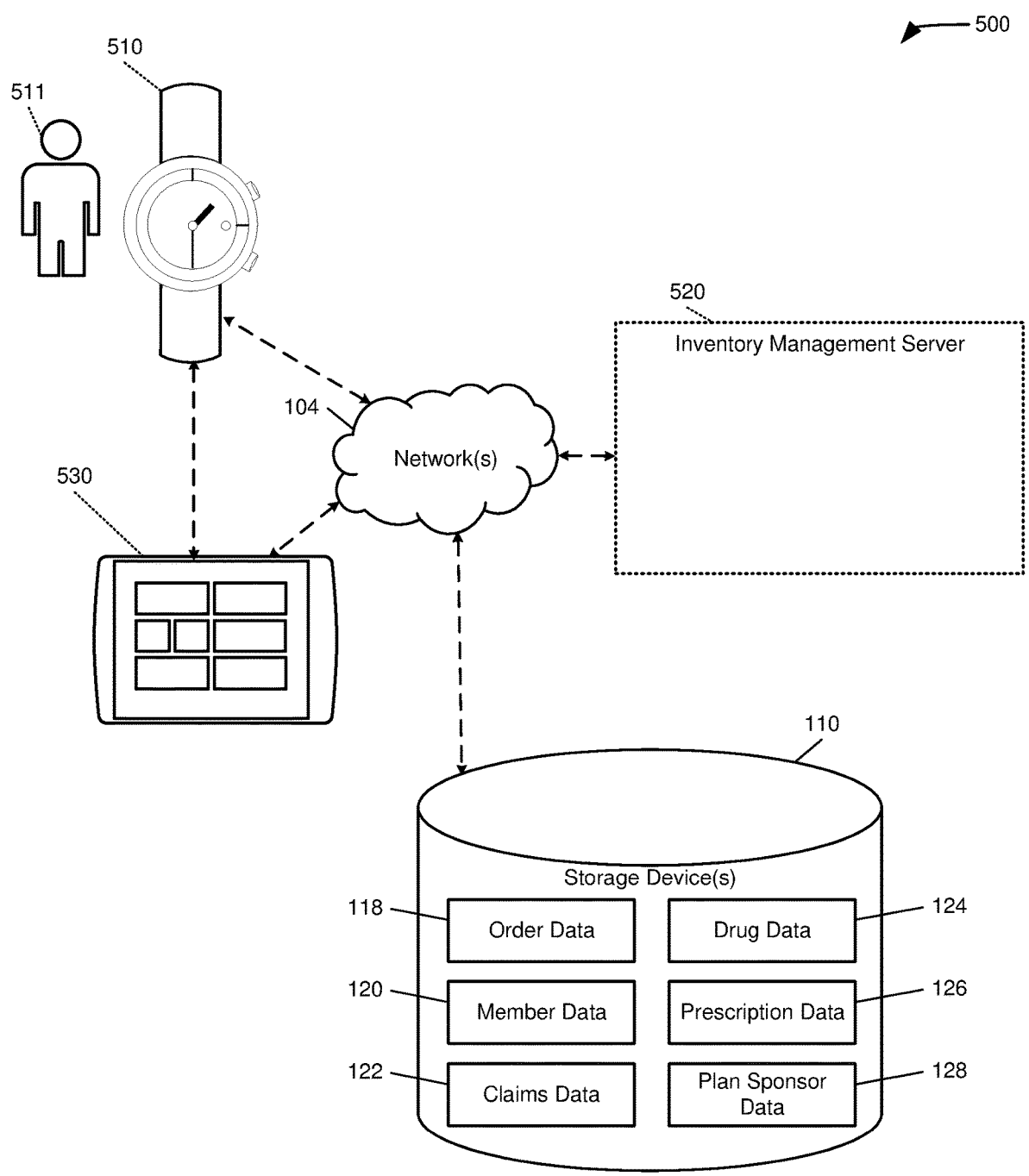
FIG. 5 is a functional block diagram of a prescription adherence system for monitoring and facilitating prescription adherence by a patient, including a wearable computing device and an inventory management server and other computing devices shown in FIG. 4.

FIG. 5 is a functional block diagram of a prescription adherence system 500 for monitoring and facilitating prescription adherence by a patient, including a wearable computing device 510 and an inventory management server and other computing devices shown in FIG. 4. Prescription adherence system 500 includes at least a wearable computing device 510 associated with a user 511 and an inventory management server 520. In some examples, prescription adherence system 500 may also include other computing devices including mobile computing device 530. In the example embodiment, devices 510, 520, and 530 each include at least a processor, memory, communications interface, and input/output in a manner similar to computing device 400 (shown in FIG. 4). As described herein, devices 510, 520, and 530 are configured to communicate with one another and with external systems via network 104. Devices 510, 520, and 530 may utilize any suitable wireless protocol for communications including but not limited to cellular communications, Bluetooth® connectivity, WiFi, near field communication (NFC), and Zigbee. In some examples, devices 510, 520, and 530 are also configured to communicate through wired networking protocols. In the example embodiment, computing devices 510 and 530 include touchscreen graphical displays configured to provide graphical user interfaces and receive user inputs. Devices 510 and 530 may include components and methods for tracking location and orientation including, for example, gyroscope, an accelerometer, and a position detector, and may be configured to receive and capture other user information including location data and orientation data. Devices 510 and 523 are also configured to receive audio input through an interface such as a microphone, and to present audio output through a speaker. Wearable computing device 510 may additionally be configured to capture user biometric information including but not limited to heart rate and electrocardiogram data. In some examples, wearable computing device 510 may be configured to capture user body temperature, blood pressure, and blood glucose levels.

In the example embodiment, devices 510 and 530 are configured to store and execute applications to facilitate the systems and methods described herein. Specifically, wearable computing device 510 executes a wearable app on its processor that is configured to present and provide the user interfaces and information described herein. Similarly, mobile computing device 530 executes a mobile app on its processor that is configured to present and provide the user interfaces and information described herein. The mobile app is a specific machine to execute a defined set of tasks.

Inventory management server 520 is also configured to aggregate, track, and compile the set of prescription plan data. In some examples, inventory management server 520 obtains the set of prescription plan data from storage devices 110 directly or via network 104. As described herein, wearable computing device 510, inventory management server 520, and mobile computing device 530 may synchronize with one another to ensure consistent tracking of data including the set of prescription plan data, adherence data, and data on renewals, refills, and other orders.

Figure 6:
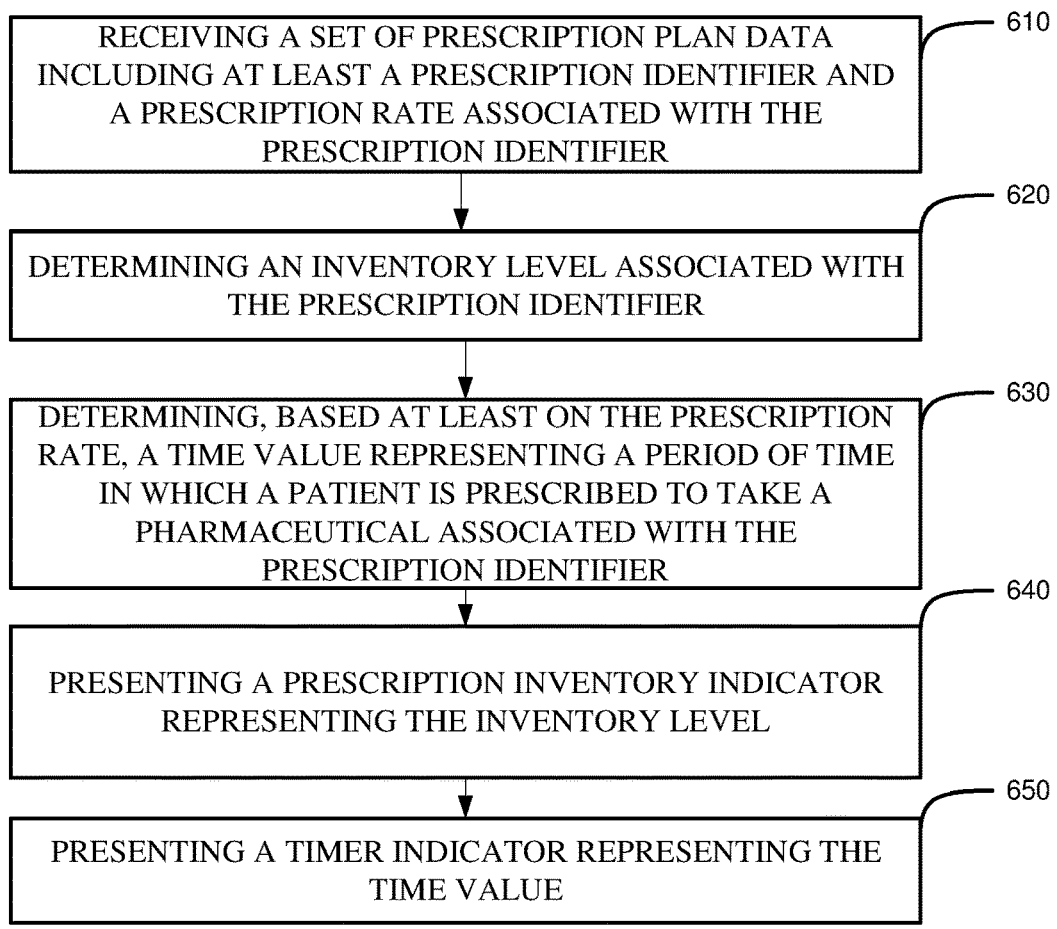
FIG. 6 is a flow diagram representing a method for monitoring and facilitating prescription adherence by a patient performed by the prescription adherence system shown in FIG. 5.

FIG. 6 is a flow diagram 600 representing a method for monitoring and facilitating prescription adherence by a patient performed by the prescription adherence system 500 shown in FIG. 5. Specifically, wearable computing device 510 is configured to receive 610 a set of prescription plan data including at least a prescription identifier and a prescription rate associated with the prescription identifier. Wearable computing device 510 is also configured to determine 620 an inventory level associated with the prescription identifier. Wearable computing device 510 is additionally configured to determine 630 based at least on the prescription rate, a time value representing a period of time in which a patient is prescribed to take a pharmaceutical associated with the prescription identifier. Wearable computing device 510 is also configured to present 640 a prescription inventory indicator representing the inventory level and to present 650 a timer indicator representing the time value.

Figure 7:
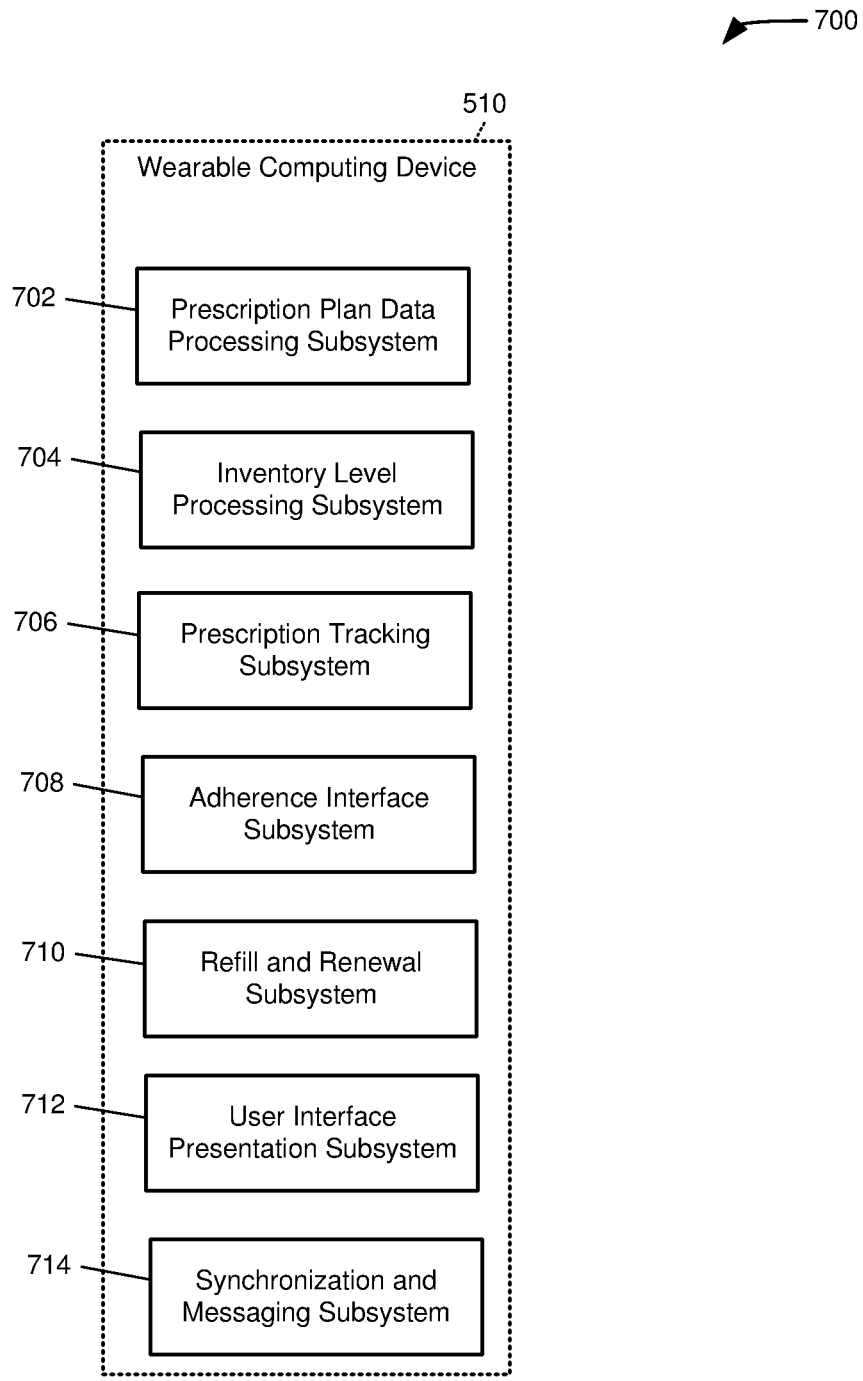
FIG. 7 is a diagram of elements of one or more example computing devices that may be used in the system shown in FIGS. 1-5.

FIG. 7 is a diagram of elements of one or more example computing devices that may be used in the system shown in FIGS. 1-5. As described herein, the elements 702, 704, 706, 708, 710, 712, and 714 are configured to perform the processes and methods described herein. The elements 702, 704, 706, 708, 710, 712, and 714 include circuitry to execute certain tasks as described herein. Prescription plan data processing subsystem 702 is configured to perform steps related to receiving a set of prescription plan data including at least a prescription identifier and a prescription rate associated with the prescription identifier. Inventory level processing subsystem 704 is configured to tracking and monitoring inventory levels for each prescribed pharmaceutical through processing user adherence data and synchronizing with inventory management server 520. Prescription tracking subsystem 706 is configured to process information related to the timing and instructions provided with each prescription. Adherence interface subsystem 708 is configured to generate and manage the adherence user interfaces as described herein. Refill and renewal subsystem 710 is configured to generate and manage the refill and renewal user interfaces, according to the methods described herein. User interface subsystem 712 is configured to generate and manage the presentation of the user interface provided on the wearable app. Synchronization and messaging subsystem 714 is configured to control communications with other devices including inventory management server 520 and to ensure that pertinent data is synchronized across devices. Synchronization and messaging server 714 also controls the presentation of alerts.

Figure 8:
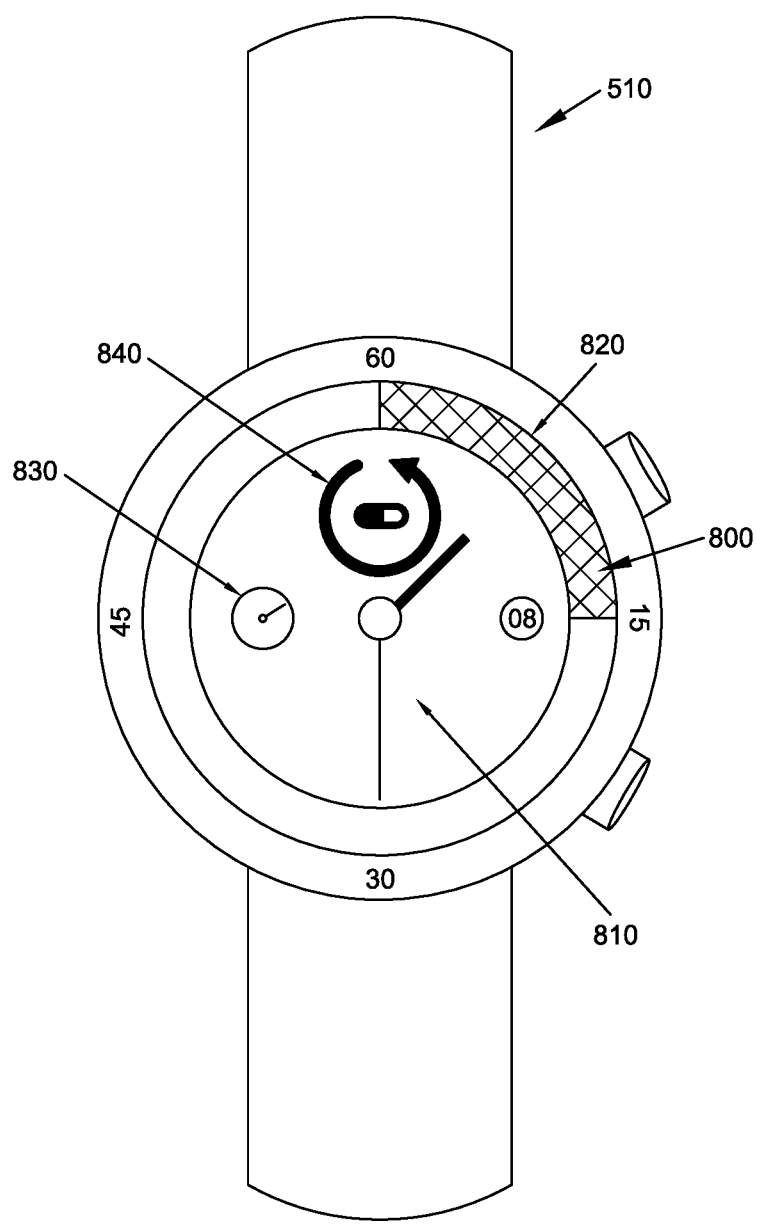
FIG. 8 depicts a first illustration of a first user interface displayed by the wearable computing device, for use in the prescription adherence system shown in FIG. 5.

FIG. 8 depicts a first illustration of the wearable computing device 510 for use in the prescription adherence system 500 (both shown in FIG. 5.) Specifically, FIG. 8 shows an example wearable computing device 510 used to monitor and facilitate adherence to prescriptions. In FIGS. 8-13, wearable computing device 510 is a smartwatch according to a first embodiment similar to a Samsung Galaxy Smartwatch, such as the Samsung Galaxy Watch Active2. Wearable computing device 510 is configured to present a user interface 800 associated with the wearable app. User interface 800 includes a clock 810. User interface 800 also includes a prescription inventory indicator 820 configured to track the amount of available prescription inventory for a first prescription associated with the user and with a first prescription identifier. In the example embodiment, prescription inventory indicator 820 is configured to decrease as a user indicates usage of a prescription. Further, in the example embodiment, prescription inventory indicator may reflect a relative scale based on the typical hours of a clock. As such, because prescription inventory indicator 820 in FIG. 8 is filled until the 3 o'clock hour, the inventory level is three. In other examples, other scales may be used as needed. The prescription inventory indicator 820 can be an arcuate graphical element that extends around the outside of the watch face adjacent the bezel. The prescription inventory indicator 820 will have a radial dimension that extends inwardly from bezel but does not overlap an interior information area of the watch face. The prescription inventory indicator 820 can be a partial annulus sector with the circumferential length being set based on the amount of refills or amount of doses left in the currently filled prescription.

User interface 800 also includes a timer indicator 830 that presents the amount of time remaining within which a patient is prescribed to take a particular pharmaceutical. Timer indicator 830 in FIG. 8 is a chronometer that counts down to zero. The prescription timer indicator 830 can be a graphical element that shows a countdown arm moved within the graphical element. The prescription timer indicator 830 will have a dimension that allows it to be positioned in the watch face interiorly of the prescription inventory indicator 820.

User interface 800 also includes a refill user interface 840 that allows a user to request a refill of a first prescription associated with the user and with a first prescription identifier. The refill user interface 840 can be a graphical element that shows a graphical element. The refill user interface 840 will have a dimension that allows it to be positioned in the watch face interiorly of the prescription inventory indicator 820. In some examples, more than one refill user interface 840 may be available. In some such examples, the refill user interfaces 840 may be displayed over more than one screen and a user may scroll to and through the refill user interfaces 840 by using any suitable input gesture including swiping or dragging.

The watchface of the wearable computing device 510 can include a plurality of hands, e.g., an hour hand and a minute hand. The hands can extend interiorly of the prescription inventory indicator 820 and over the prescription timer indicator 830 and the refill user interface 840. In another example, the hands can extend over the prescription inventory indicator 820 to the bezel, e.g., with distinctive colors relative to the prescription inventory indicator 820.

In an example embodiment, the watchface of the wearable computing device 510 includes a digital time readout interiorly of the prescription inventory indicator 820 and over the prescription timer indicator 830 and the refill user interface 840.

Figure 9:
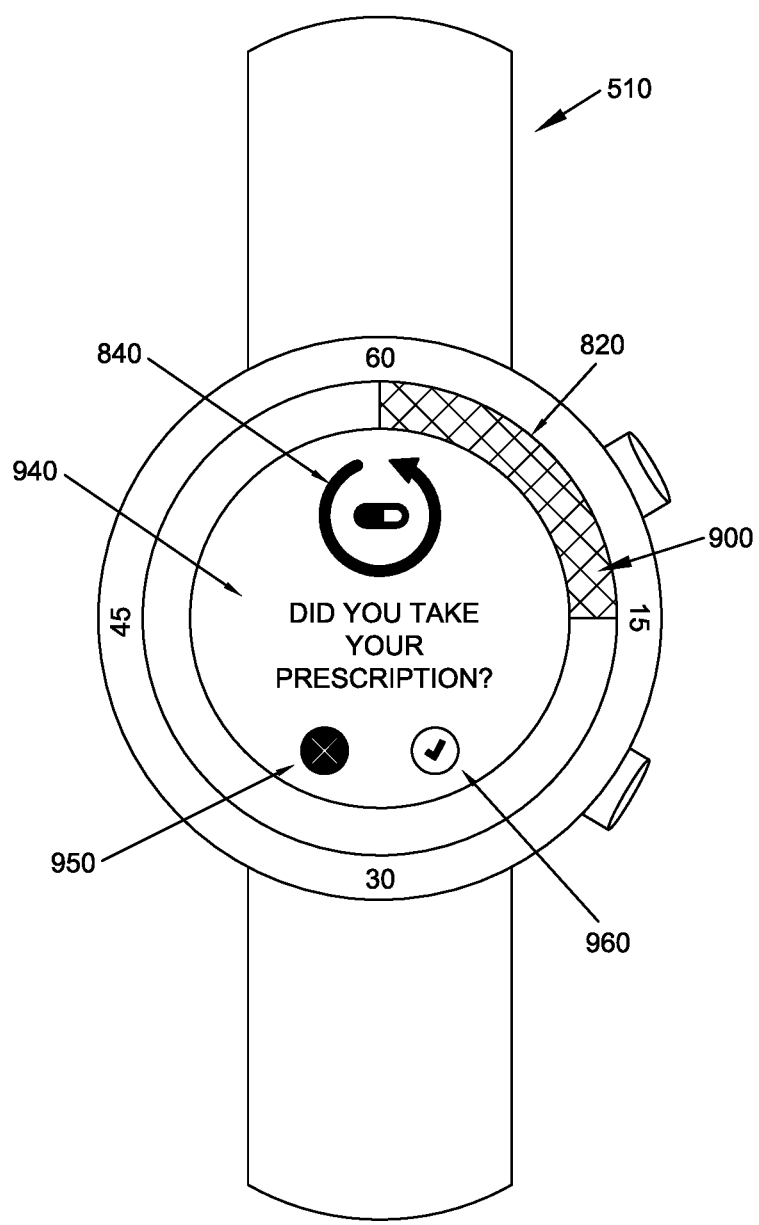
FIG. 9 depicts a second illustration of a first user interface displayed by the wearable computing device, for use in the prescription adherence system shown in FIG. 5.

FIG. 9 depicts a second illustration the wearable computing device 510 for use in the prescription adherence system 500 (both shown in FIG. 5). In FIG. 9, wearable computing device 510 is a smartwatch similar to a Samsung Galaxy Smartwatch. Wearable computing device 510 displays user interface 900 for the wearable app. Specifically, user interface 900 depicts an adherence user interface configured to receive input to confirm whether the patient has taken the pharmaceutical. In operation, an adherence user interface is presented to a user when timer indicator 830 (shown in FIG. 8) counts to zero, indicating that a pharmaceutical is prescribed to be taken. Additionally, user interface 900 may be presented a user requests to provide adherence data because the user wishes to take a particular pharmaceutical before timer indicator 830 counts to zero. Wearable computing device 510 may be configured to allow a user to provide adherence data when a user selects timer indicator 830 before it counts to zero. User interface 900 includes a request message 940 asking the patient to confirm if they took their prescription, a no input 950, and a yes input 960. User interface 900 is therefore configured to capture adherence data based on a user selection of inputs 950 or 960. User interface 900 also displays prescription inventory indicator 820 and refill user interface 840.

Figure 10:
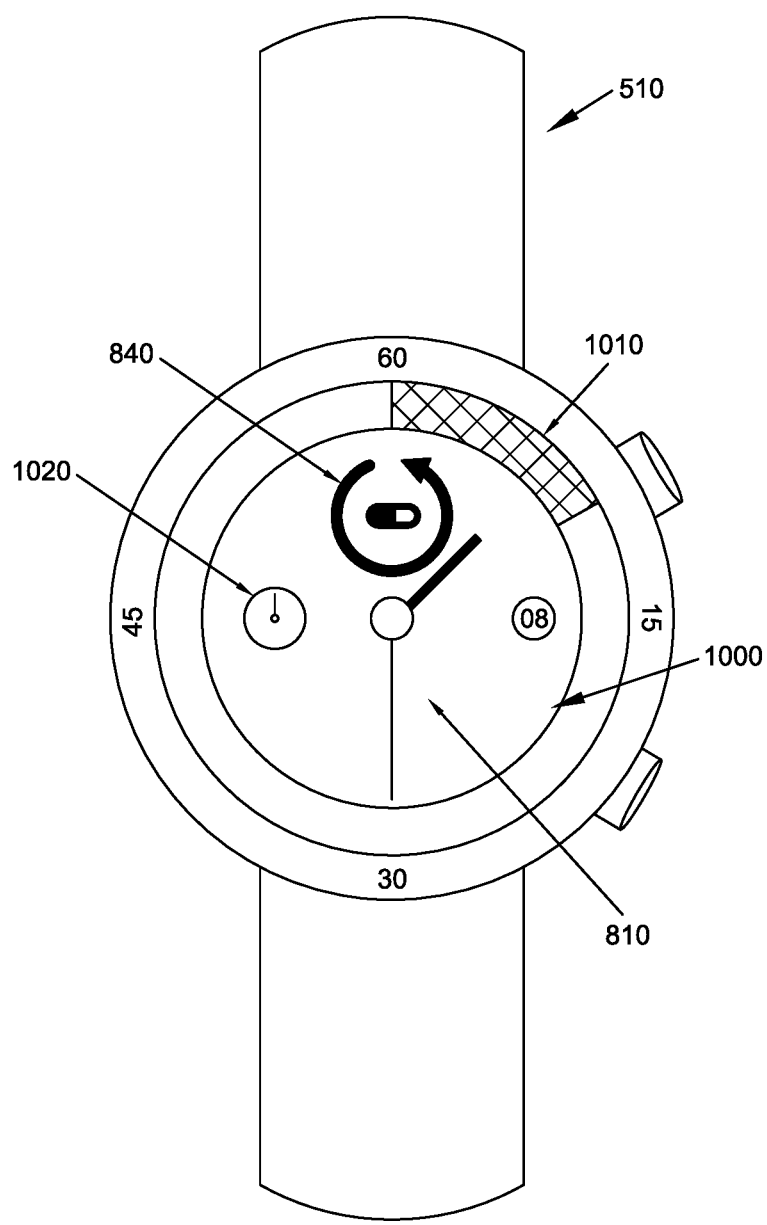
FIG. 10 depicts a third illustration of a first user interface displayed by the wearable computing device, for use in the prescription adherence system shown in FIG. 5.

FIG. 10 depicts a third illustration the wearable computing device 510 for use in the prescription adherence system 500 (both shown in FIG. 5.) In FIG. 10, wearable computing device 510 is a smartwatch similar to a Samsung Galaxy Smartwatch. Wearable computing device 510 displays user interface 1000 for the wearable app after a user selects input 960 to confirm that they took a prescription pharmaceutical at the prompted time and adhered to the prescription. As such, prescription inventory indicator 1010 is relatively lower than prescription inventory indicator 820 because it has been decremented and timer indicator 1020 has reset and is counting down to zero again. Per the convention identified above (scaled to the hours of a clock), prescription inventory indicator 1010 may indicate that the inventory level is two doses. In other examples, other scales may be used as needed. User interface 1000 also displays clock 810 and refill user interface 840.

Figure 11:
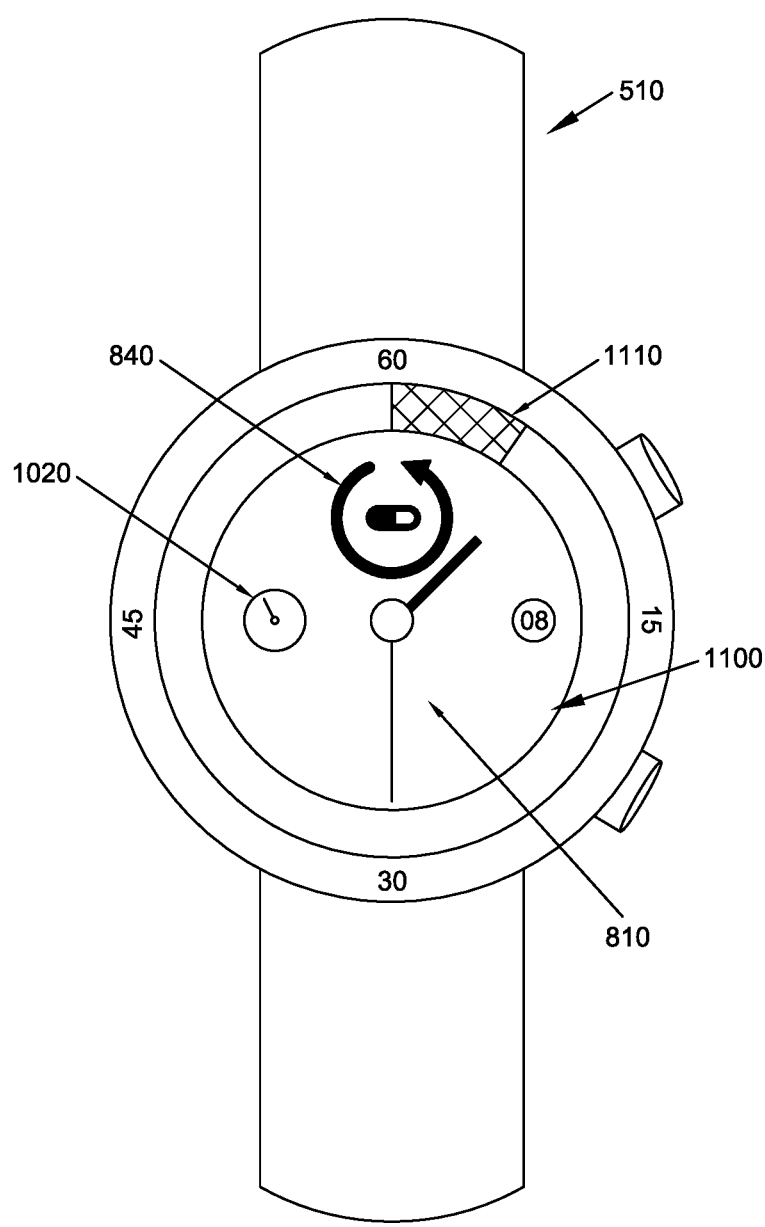
FIG. 11 depicts a fourth illustration of a first user interface displayed by the wearable computing device, for use in the prescription adherence system shown in FIG. 5.

FIG. 11 depicts a fourth illustration the wearable computing device 510 for use in the prescription adherence system 500 (both shown in FIG. 5.) In FIG. 11, wearable computing device 510 is a smartwatch similar to a Samsung Galaxy Smartwatch. Wearable computing device 510 displays user interface 1100 as shown after a user again confirms that they took a prescription pharmaceutical at the prompted time and adhered to the prescription. As such, prescription inventory indicator 1110 is relatively lower than prescription inventory indicator 1010 because it has been decremented and timer indicator 1120 has reset and is counting down to zero again. Per the convention identified above (scaled to the hours of a clock), prescription inventory indicator 1010 may indicate that the inventory level is one dose. In other examples, other scales may be used as needed. User interface 1100 also displays clock 810 and refill user interface 840.

Figure 12:
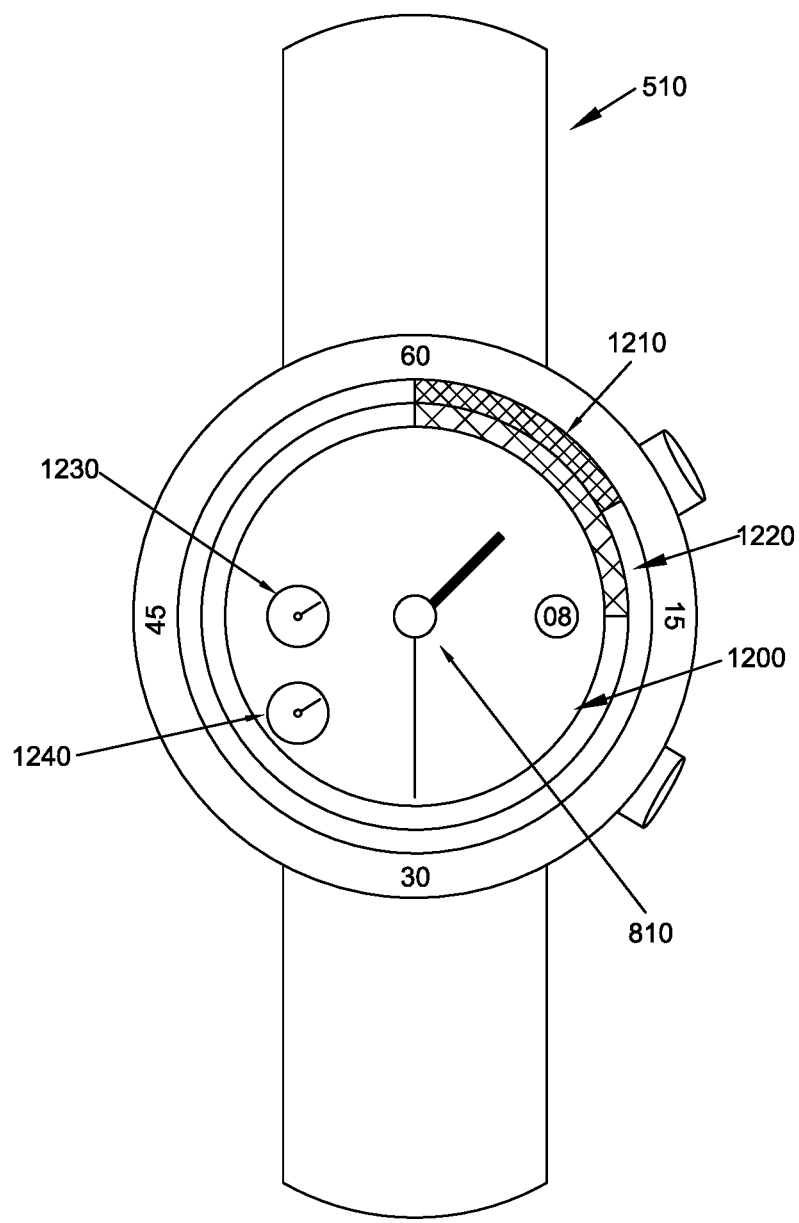
FIG. 12 depicts a fifth illustration of a first user interface displayed by the wearable computing device, for use in the prescription adherence system shown in FIG. 5.
Figure 13:
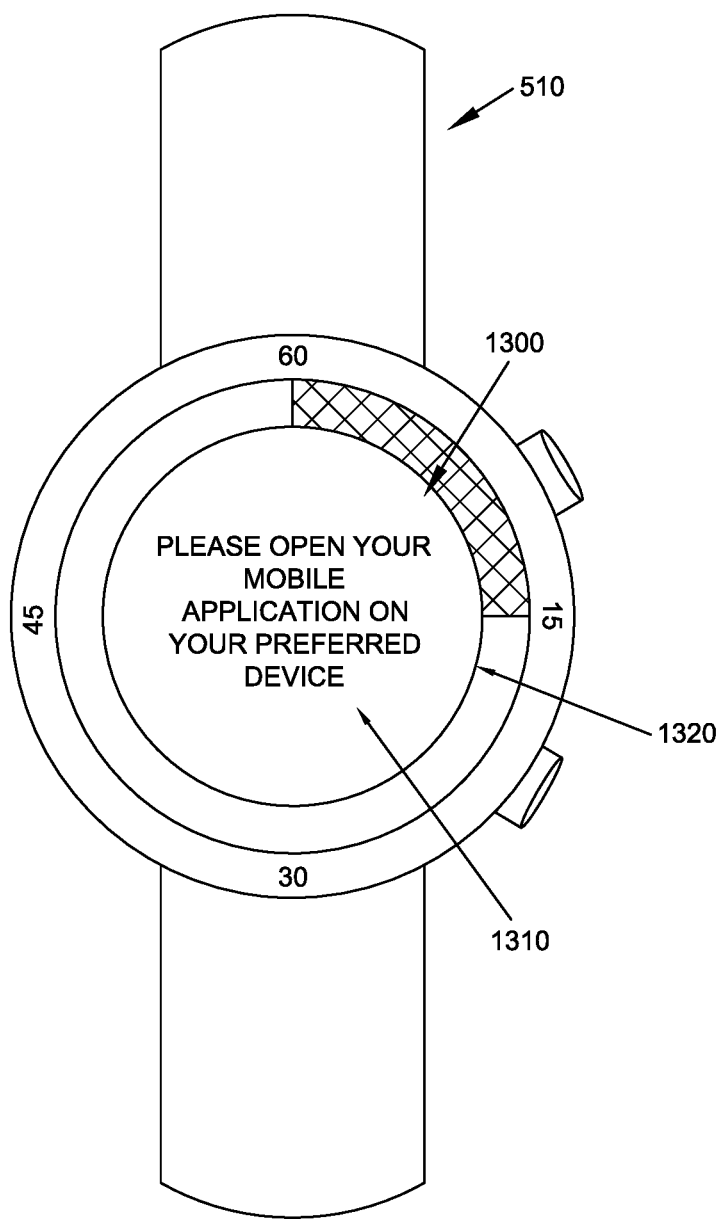
FIG. 13 depicts a sixth illustration of a first user interface displayed by the wearable computing device, for use in the prescription adherence system shown in FIG. 5.

FIG. 12 depicts a fifth illustration the wearable computing device 510 for use in the prescription adherence system 500 (both shown in FIG. 5.) In FIG. 12, wearable computing device 510 is a smartwatch similar to a Samsung Galaxy Smartwatch. Wearable computing device 510 displays user interface 1200 which includes tracking for multiple prescriptions. As described above, wearable computing device 510 may be configured to display information on multiple prescriptions so that a user can track and monitor their prescription adherence for more complex prescription plans. User interface 1200 accordingly displays two distinct prescription inventory indicators 1210 and 1220 and two timer indicators 1230 and 1240. In an example embodiment, the user interface 1200 can include one or more, e.g., two refill user interfaces that can be selected to trigger a refill graphical user interface. In some examples, where multiple prescriptions are tracked on wearable computing device 510, elements such as refill user interfaces may not be displayed on this screen, and instead presented on an adherence screen such as the one shown in user interface 900 (shown in FIG. 9). In other examples, wearable computing device 510 may present information and interfaces for additional prescriptions. In the example embodiment, each of elements 1210, 1220, 1230, and 1240 is color coded based on user preference as indicated on either the mobile app (using a computing device such as mobile computing device 530 shown in FIG. 5) or the wearable app. If a refill user interface is shown on the user interface, then the refill user interface is color coded to the user preference FIG. 13 depicts a sixth illustration the wearable computing device 510 for use in the prescription adherence system 500 (both shown in FIG. 5.) In FIG. 13, wearable computing device 510 is a smartwatch similar to a Samsung Galaxy Smartwatch. Wearable computing device 510 displays user interface 1300 as presented after a user has selected a refill user interface such as refill user interface 1250 or 1260 (shown in FIG. 12) and the user is prompted to open a mobile app (using a computing device such as mobile computing device 530 shown in FIG. 5) to authenticate the refill request. The mobile computing device 530 may push other notifications to the watchface 1320 for display within user interface 1300 to the user.

Figure 14:
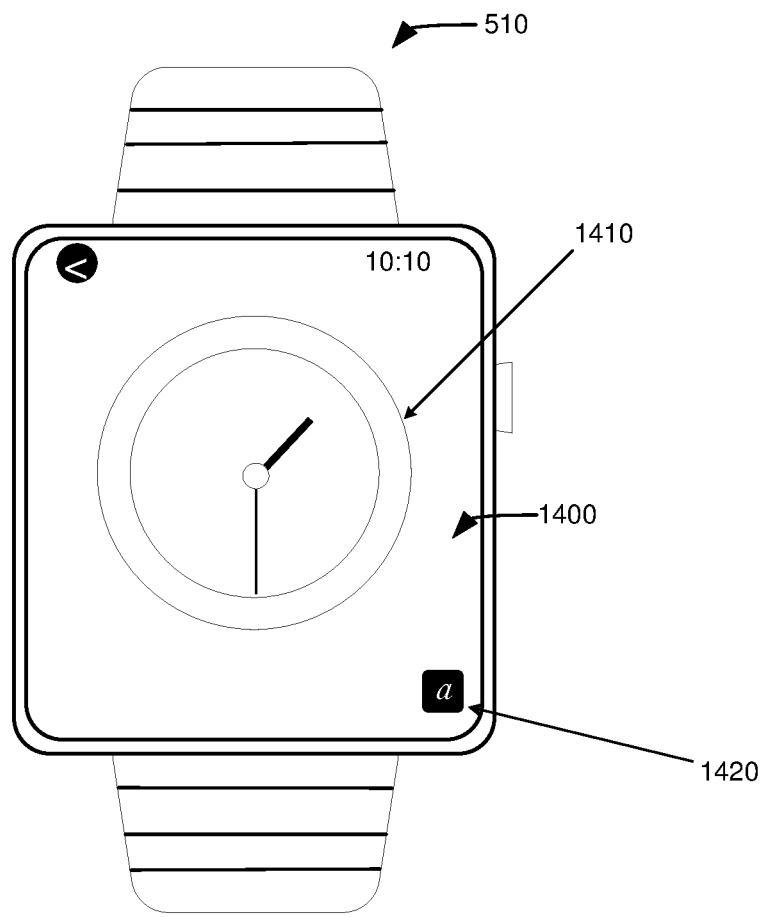
FIG. 14 depicts a first illustration of a second user interface displayed by the wearable computing device, for use in the prescription adherence system shown in FIG. 5.
Figure 15:
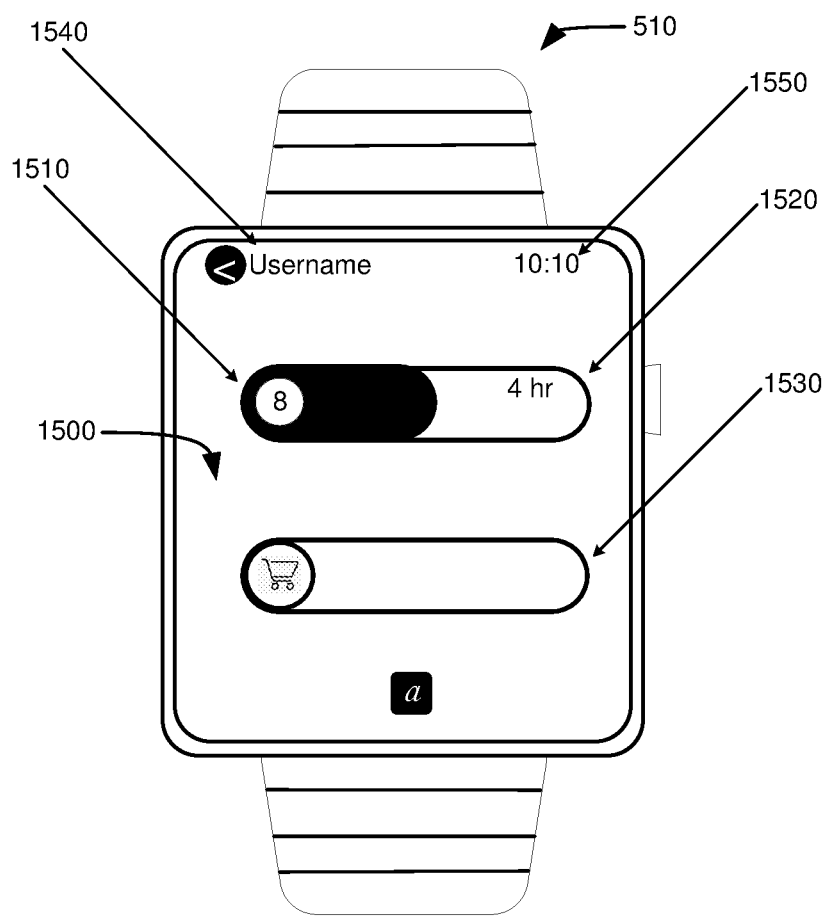
FIG. 15 depicts a second illustration of a second user interface displayed by the wearable computing device, for use in the prescription adherence system shown in FIG. 5.
Figure 16:
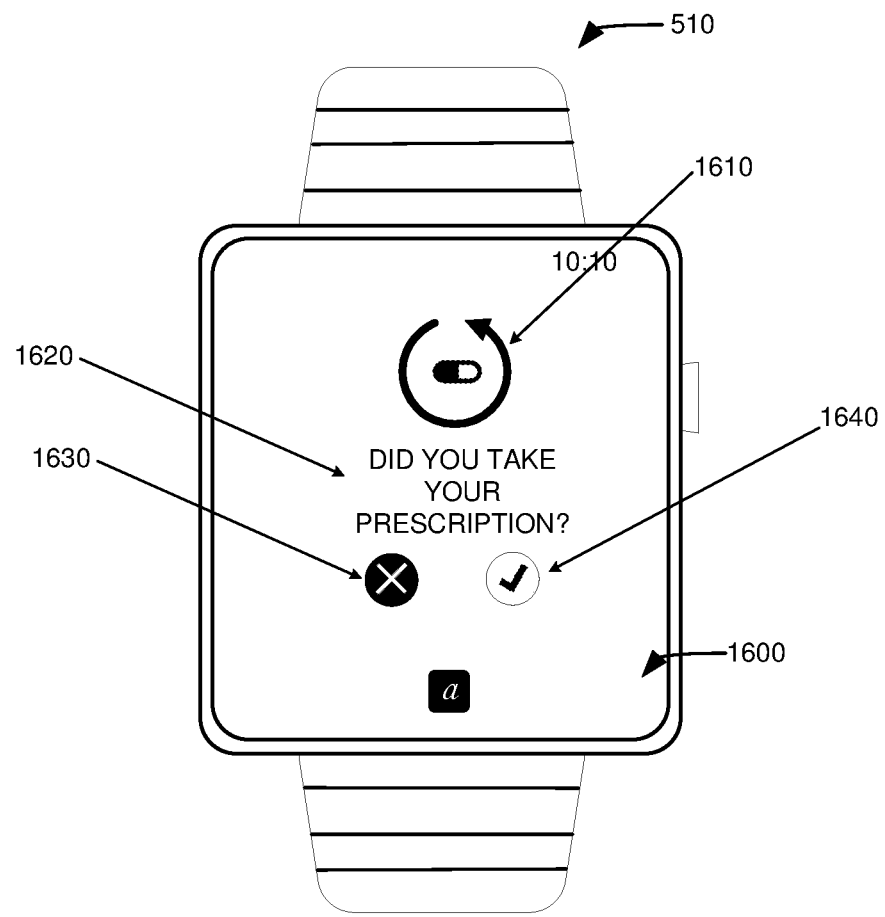
FIG. 16 depicts a third illustration of a second user interface displayed by the wearable computing device, for use in the prescription adherence system shown in FIG. 5.

FIG. 14 depicts a first illustration of the wearable computing device 510 for use in the prescription adherence system 500 (both shown in FIG. 5.) Specifically, FIG. 14 shows an example wearable computing device 510 used to monitor and facilitate adherence to prescriptions according. In FIGS. 14-16, wearable computing device 510 is a smartwatch according to a second embodiment similar to an Apple Watch. In FIG. 14, wearable computing device 510 presents a user interface 1400 including a clock 1410 and a prescription adherence selection icon 1420. In FIG. 14, a user may access the wearable app by selecting icon 1420.

FIG. 15 depicts a second illustration of the wearable computing device 510 for use in the prescription adherence system 500 (both shown in FIG. 5). In FIG. 15, wearable computing device 510 is a smartwatch similar to an Apple Watch. Wearable computing device 510 presents user interface 1500 depicts a primary user interface for the wearable app. User interface 1500 includes prescription inventory indicator 1510 (indicating that eight doses are available), timer indicators 1520 (indicating that four hours remain within which the patient must take a prescribed pharmaceutical), and refill user interface 1530. User interface 1500 also includes user information area 1540 and clock 1550.

FIG. 16 depicts a third illustration of the wearable computing device 510 for use in the prescription adherence system 500 (both shown in FIG. 5). In FIG. 16, wearable computing device 510 is a smartwatch similar to an Apple Watch. Specifically, user interface 1600 depicts an adherence user interface configured to receive input to confirm whether the patient has taken the pharmaceutical. In operation, an adherence user interface is presented to a user when timer indicator 1520 (shown in FIG. 15) counts to zero, indicating that a pharmaceutical is prescribed to be taken. Additionally, user interface 1600 may be presented a user requests to provide adherence data because the user wishes to take a particular pharmaceutical before timer indicator 1520 counts to zero. Wearable computing device 510 may be configured to allow a user to provide adherence data when a user selects timer indicator 1520 before it counts to zero. User interface 1600 includes a request message 1620 asking the patient to confirm if they took their prescription, a no input 1630, and a yes input 1640. User interface 1600 is therefore configured to capture adherence data based on a user selection of inputs 1630 or 1650. User interface 1600 also displays refill user interface 1610.

The user interfaces presented in FIGS. 8-16 are for illustrative purposes only. In other examples, other user interfaces may be used to provide the systems and methods described.

Figure 17:
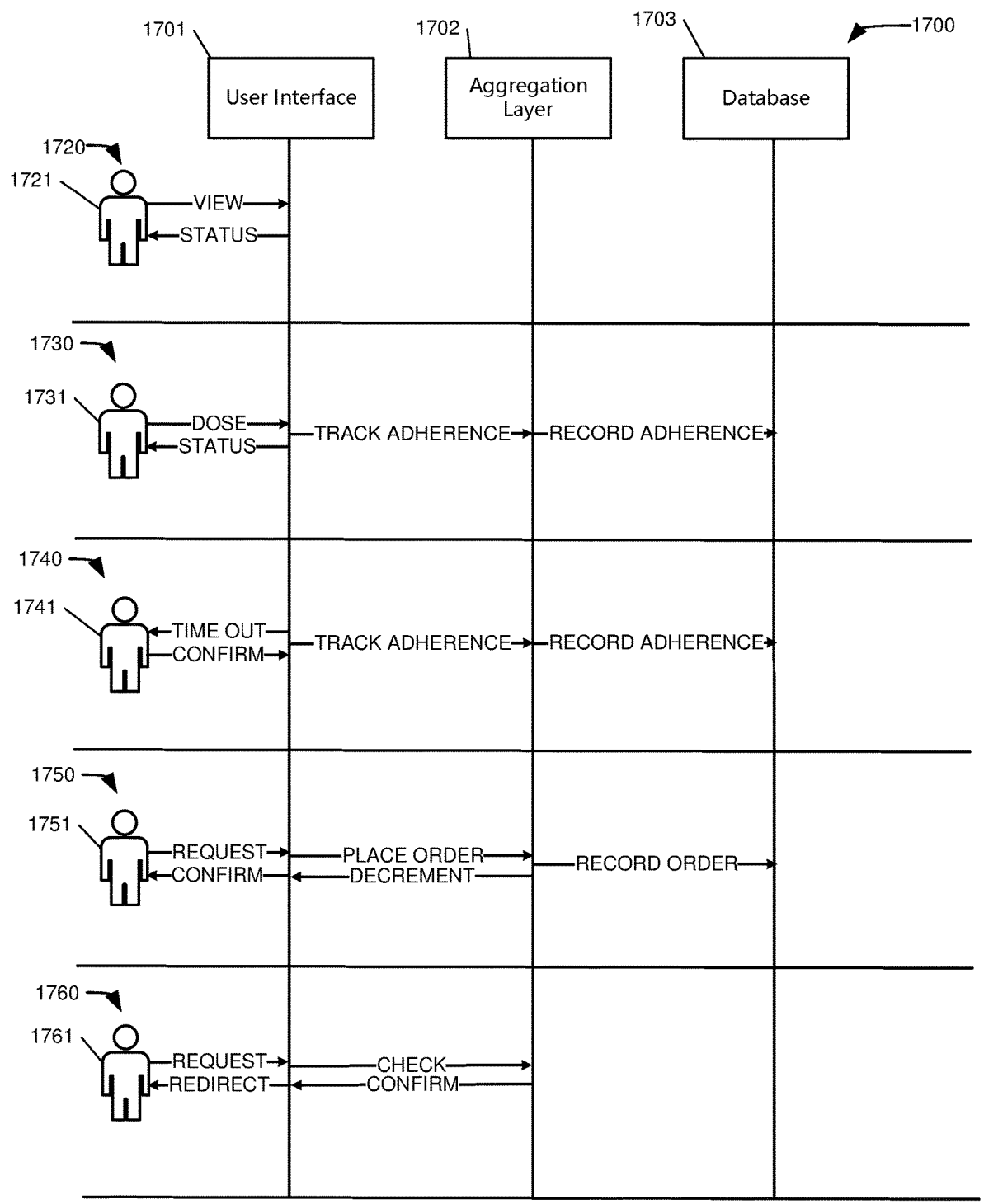
FIG. 17 depicts a set of example use cases that may be performed using the prescription adherence system for monitoring and facilitating prescription adherence by a patient, including a wearable computing device and an inventory management server and other computing devices shown in FIG. 4.

FIG. 17 depicts a set 1700 of example use cases 1720, 1730, 1740, 1750, and 1760 that may be performed using the prescription adherence system 500 (shown in FIG. 5) for monitoring and facilitating prescription adherence by a patient.

Described in set 1700 are use cases 1720, 1730, 1740, 1750, and 1760 that may be performed using the prescription adherence system 500. Notably, wearable computing device 510 (shown in FIG. 5) facilitates at least five distinct use cases 1720, 1730, 1740, 1750, and 1760 for monitoring and promoting prescription adherence. Use cases 1720, 1730, 1740, 1750, and 1760 are performed by users 1721, 1731, 1741, 1751, and 1761. Users 1721, 1731, 1741, 1751, and 1761 perform the use cases by using wearable computing device 510 displaying user interface 1701 which collects information and input into aggregation layer 1702 on a memory such as memory 412 (shown in FIG. 4) and which may record information in database 1703. In the example embodiment, database 1703 may reside in any suitable system including but not limited to storage device 110 and inventory management server 520 (both shown in FIG. 5).

In first use case 1720, wearable computing device 510 is configured to provide inventory and timing information for a plurality of prescriptions. More specifically, wearable computing device 510 receives a set of prescription plan data for a plurality of prescriptions including prescription identifiers and prescription rates for each prescription identifier. Wearable computing device 510 determines, for each prescribed pharmaceutical, an inventory level and a time value indicating a period of time in which the patient is prescribed to take each prescribed pharmaceutical. Accordingly, as shown in use case 1720, user 1721 views wearable computing device 510 which displays (or presents) a status including an inventory indicator representing the inventory level for each prescribed pharmaceutical and a time indicator representing the time value for each prescribed pharmaceutical. In use case 1720, wearable computing device 510 regularly updates user 1721 about the status of each of her or his prescribed prescriptions that are tracked by wearable computing device 510. In some cases, user 1721 may have enough prescriptions to cause wearable computing device 510 to display prescription inventories and timer indicators over multiple display screens through which a user may toggle or scroll. User 1721 may configure the order and orientation of such prescription inventories and timer indicators based on user preference. In the example embodiment, user 1721 configures the order and orientation through use of the mobile app. In other embodiments, user 1721 may configure the order and orientation using the wearable app.

In a second use case 1730, wearable computing device 510 tracks adherence and records adherence. Specifically, wearable computing device 510 is configured to track the time value and prompt user 1731 to take each prescription at an appropriate time as determined by each prescription rate. Wearable computing device 510 also prompts user 1731 for adherence feedback through adherence user interface 1701 that indicates whether user 1731 has taken a prescription at the prompted time. If user 1731 adheres to the prescription and indicates the same through adherence user interface

1701, the wearable app tracks the adherence, decrements the inventory level accordingly, and presents an updated prescription inventory indicator and a reset timer indicator. The wearable app may also communicate the adherence to the inventory management server 520 or other computing devices including mobile computing device 530 (shown in FIG. 5). If user 1731 fails to adhere to the prescription and indicates the same through the adherence user interface 1701, the wearable app tracks the failed adherence, transmits an alert, presents the inventory indicator without a change (i.e., without decrementing), and presents the timer indicator to remind user 1731 that a prescription should still be taken promptly. The wearable app may transmit the alert to any suitable recipient including the inventory management server or a healthcare provider. In some cases, when wearable computing device 510 prompts user 1731 to take a particular prescribed pharmaceutical, wearable computing device 510 may provide appropriate dosage instructions or recommendations associated with the prescription such as drinking fluids or eating.

In a third user case 1740, wearable computing device 510 may track adherence without prompting user 1741 for adherence feedback. For example, user 1741 may wish to take a prescription within an appropriate window of time, but before the timer indicator reaches zero. In such examples, user 1741 may select an adherence interface icon on user interface 1701, for the appropriate prescription, and provide input indicating that user 1741 has adhered to the particular prescription. In such cases, wearable computing device 510 receives adherence feedback indicating that the patient adhered to the particular prescription, decrements the inventory level accordingly, and presents an updated prescription inventory indicator and a reset timer indicator. The wearable app may also communicate the adherence to inventory management server 520 or other computing devices including mobile computing device 530.

In fourth user case 1750, wearable computing device 510 presents a refill user interface within user interface 1701 that allows user 1751 to place a refill order. In one example, wearable computing device 510 presents the refill user interface (within user interface 1701) on the wearable app at all times and user 1751 may select it at any time. In another example, wearable computing device 510 presents the refill user interface after determining that the associated inventory level has fallen below a predefined renewal threshold indicating that user 1751 has a limited amount of prescription pharmaceutical inventory available. In some cases, the predefined renewal threshold may be associated with the time to provide or ship a refill, and therefore set to ensure that user 1751 that requests a timely refill does not run out of prescriptions while waiting for a refill. For example, the predefined renewal threshold may be calculated by wearable computing device 510 and/or the inventory management server 520 based on the expected shipping time associated with the refill, the current inventory level, and the prescription rate. Wearable computing device 510 presents the refill user interface (within user interface 1701) such that, when user 1751 requests a refill, an order is transmitted to the inventory management server and an order is recorded and noted on both the inventory management server and on wearable computing device 510. When the inventory management server receives the refill order, in some examples it transmits a confirmation to wearable computing device 510 and other associated devices that indicates that the order fulfillment is in progress. Wearable computing device 510 is also configured to present the amount of available refills on or in conjunction with the presentation of the refill user interface. When the confirmation of order fulfillment is received by wearable computing device 510, wearable computing device 510 decrements the amount of available refills available and revises the refill user interface to present a decremented amount of available refills.

In a fifth use case 1760, wearable computing device 510 is configured to allow user 1761 to request a renewal of a prescription through the use of a renewal user interface within user interface 1701. In one example, wearable computing device 510 presents the renewal user interface (within user interface 1701) on the wearable app at all times and user 1761 may select it at any time. In another example, wearable computing device 510 presents the renewal user interface after determining that the amount of available renewals has fallen below a predefined renewal threshold. In the example embodiment, wearable computing device 510 presents the renewal interface when the amount of available refills is at one or fewer. Wearable computing device 510 presents the renewal user interface to allow a renewal request. When the renewal user interface receives a renewal request, wearable computing device 510 transmits a confirmation request to inventory management server 520 to confirm that a renewal of the prescription is available. When inventory management server 520 confirms that a renewal of the prescription is available, user 1761 may complete a request for renewal. In some examples, wearable computing device 510 redirects user 1761 to the mobile computing device or another suitable device so that user 1761 may complete the request for renewal on the mobile app. If the inventory management server determines a renewal of the prescription is not available, it transmits an unavailability message to wearable computing device 510. If wearable computing device 510 receives an unavailability message, wearable computing device 510 causes the wearable app to present an alert to user 1761 indicating that no renewals are available.

The described use cases are presented for illustrative purposes. In other examples, other use cases of the systems and methods described herein may be provided by combining or adapting any of the described steps or any of the examples together.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The foregoing description generally describes the wearable device in various embodiments as a watch, however, other wearables are within the scope of the present disclosure. Other examples of the wearable include bracelets or other personal accessories that are worn on a limb, and clothing. The graphical display can be secured in clothing, e.g., a sleeve, vest or flap of fabric.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP:

Hypertext Preprocessor), Scala, Eiffel, Smalltalk, Erlang, Ruby, Flash®, Visual Basic®, Lua, MATLAB, SIMULINK, and Python®.

What is claimed is:

1. A method for monitoring prescription adherence performed by a wearable computing device in communication with an inventory management server, the wearable computing device including a processor and a memory, the method comprising:
   receiving a set of prescription plan data including at least a prescription identifier and a prescription rate associated with the prescription identifier;
   determining an inventory level associated with the prescription identifier;
   determining, based at least on the prescription rate, a time value representing a period of time in which a patient is prescribed to take a pharmaceutical associated with the prescription identifier;
   presenting, by the wearable computing device to a user, a prescription inventory indicator representing the inventory level;
   presenting, by the wearable computing device to the user, a timer indicator representing the time value, wherein presenting, by the wearable computing device to the user, the timer indicator includes presenting the timer indicator in an interior information area of the wearable computing device;
   receiving an inventory update from the inventory management server;
   revising the inventory level based on the inventory update; and
   presenting, by the wearable computing device to the user, the prescription inventory indicator representing the revised inventory level, wherein presenting, by the wearable computing device to the user, the prescription inventory indicator representing the revised inventory level includes presenting the prescription inventory indicator as a scaled, arcuate graphical element adjacent a bezel of the wearable computing device and not overlapping the interior information area such that the wearable computing device displays a second graphical element in the interior information area.

2. The method of claim 1, further comprising:
   determining that the time value indicates that the patient is prescribed to take the pharmaceutical immediately;
   presenting an adherence user interface configured to receive input to confirm whether the patient has taken the pharmaceutical; and
   receiving input from the user confirming whether the patient has taken the pharmaceutical.

3. The method of claim 2, further comprising:
   determining, based on the input, that the patient has taken the pharmaceutical;
   decrementing the inventory level based on the input;
   resetting the time value to the period of time associated with the prescription rate;
   presenting the prescription inventory indicator representing the inventory level; and
   presenting the timer indicator representing the time value.

4. The method of claim 2, further comprising:
   determining, based on the input, that the patient has not taken the pharmaceutical;
   transmitting an alert message;
   presenting the prescription inventory indicator representing the inventory level; and
   presenting the timer indicator representing the time value.

5. The method of claim 1, further comprising:
   synchronizing the time value and the inventory level with the inventory management server.

6. The method of claim 1, further comprising:
   presenting a refill user interface configured to receive a refill input requesting a resupply of the prescription associated with the prescription indicator; and
   upon receiving the refill input, transmitting a refill request to the inventory management server.

7. A wearable computing device in communication with an inventory management server, the wearable computing device comprising a processor and a memory, wherein the processor is configured to:
   receive a set of prescription plan data including at least a prescription identifier and a prescription rate associated with the prescription identifier;
   determine an inventory level associated with the prescription identifier;
   determine, based at least on the prescription rate, a time value representing a period of time in which a patient is prescribed to take a pharmaceutical associated with the prescription identifier;
   present, by the wearable computing device to a user, a prescription inventory indicator representing the inventory level;
   present, by the wearable computing device to the user, a timer indicator representing the time value in an interior information area of the wearable computing device;
   receive an inventory update from the inventory management server;
   revise the inventory level based on the inventory update; and
   present, by the wearable computing device to the user, the prescription inventory indicator representing the revised inventory level as a scaled, arcuate graphical element adjacent a bezel of the wearable computing device and not overlapping the interior information area such that the wearable computing device displays a second graphical element in the interior information area.

8. The wearable computing device of claim 7, wherein the processor is further configured to:
   determine that the time value indicates that the patient is prescribed to take the pharmaceutical immediately;
   present an adherence user interface configured to receive input to confirm whether the patient has taken the pharmaceutical; and
   receive input from the user confirming whether the patient has taken the pharmaceutical.

9. The wearable computing device of claim 8, wherein the processor is further configured to:
   determine, based on the input, that the patient has taken the pharmaceutical;
   decrement the inventory level based on the input;
   reset the time value to the period of time associated with the prescription rate;
   present the prescription inventory indicator representing the inventory level; and
   present the timer indicator representing the time value.

10. The wearable computing device of claim 8, wherein the processor is further configured to:
   determine, based on the input, that the patient has not taken the pharmaceutical;
   transmit an alert message;
   present the prescription inventory indicator representing the inventory level; and
   present the timer indicator representing the time value.

11. The wearable computing device of claim 7, wherein the processor is further configured to:
  synchronize the time value and the inventory level with the inventory management server.

12. The wearable computing device of claim 7, wherein the processor is further configured to:
  present a refill user interface configured to receive a refill input requesting a resupply of the prescription associated with the prescription indicator; and
  upon receiving the refill input, transmit a refill request to the inventory management server.

13. A prescription adherence system for monitoring and facilitating prescription adherence by a patient comprising:
  an inventory management server comprising a server processor and a server memory; and
  a wearable computing device in networked communication with the inventory management server, wherein the wearable computing device comprises a device processor and a device memory, wherein the device processor is configured to:
    receive a set of prescription plan data including at least a prescription identifier and a prescription rate associated with the prescription identifier;
    determine an inventory level associated with the prescription identifier;
    determine, based at least on the prescription rate, a time value representing a period of time in which a patient is prescribed to take a pharmaceutical associated with the prescription identifier;
    present, by the wearable computing device to a user, a prescription inventory indicator representing the inventory level; and
    present, by the wearable computing device to the user, a timer indicator representing the time value;
    receive an inventory update from the inventory management server;
    revise the inventory level based on the inventory update; and
    present, by the wearable computing device to the user, the prescription inventory indicator representing the revised inventory level as a scaled, partial annulus sector graphical element adjacent an exterior of a display of the wearable computing device; and
    present a second graphical element in an interior information area of the display of the wearable computing device with the prescription inventory indicator not overlapping the second graphical element.

14. The prescription adherence system of claim 13, wherein the device processor is configured to:
  determine that the time value indicates that the patient is prescribed to take the pharmaceutical immediately;
  present an adherence user interface configured to receive input to confirm whether the patient has taken the pharmaceutical; and
  receive input from the user confirming whether the patient has taken the pharmaceutical.

15. The prescription adherence system of claim 14, wherein the device processor is configured to:
  determine, based on the input, that the patient has taken the pharmaceutical;
  decrement the inventory level based on the input;
  reset the time value to the period of time associated with the prescription rate;
  present the prescription inventory indicator representing the inventory level; and
  present the timer indicator representing the time value.

16. The prescription adherence system of claim 14, wherein the device processor is configured to:
  determine, based on the input, that the patient has not taken the pharmaceutical;
  transmit an alert message;
  present the prescription inventory indicator representing the inventory level; and
  present the timer indicator representing the time value.

17. The prescription adherence system of claim 13, wherein the device processor is configured to:
  synchronize the time value and the inventory level with the inventory management server.

18. The prescription adherence system of claim 13, wherein the device processor is configured to:
  present a refill user interface configured to receive a refill input requesting a resupply of the prescription associated with the prescription indicator; and
  upon receiving the refill input, transmit a refill request to the inventory management server.

* * * * *